(12) United States Patent
Kourtis et al.

(10) Patent No.: US 11,110,200 B2
(45) Date of Patent: *Sep. 7, 2021

(54) IONIC POLYMER COMPOSITIONS

(71) Applicant: Hyalex Orthopaedics, Inc., Lexington, MA (US)

(72) Inventors: Iraklis Kourtis, Arlington, MA (US); Jun Li, Winchester, MA (US); Lampros Kourtis, Cambridge, MA (US)

(73) Assignee: Hyalex Orthopaedics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/091,787

(22) Filed: Nov. 6, 2020

(65) Prior Publication Data

US 2021/0052773 A1 Feb. 25, 2021

Related U.S. Application Data

(63) Continuation of application No. 16/514,279, filed on Jul. 17, 2019, now Pat. No. 10,869,950, which is a (Continued)

(51) Int. Cl.
*A61L 27/34* (2006.01)
*A61L 27/48* (2006.01)
(Continued)

(52) U.S. Cl.
CPC .......... *A61L 27/34* (2013.01); *A61F 2/0095* (2013.01); *A61F 2/3099* (2013.01);
(Continued)

(58) Field of Classification Search
CPC .. A61F 2/0095; A61F 2/30756; A61F 2/4225; A61F 2/3872; A61F 2/4081;
(Continued)

(56) References Cited

U.S. PATENT DOCUMENTS 3,030,327 A 4/1962 Hosch
3,053,251 A 9/1962 Black et al.
(Continued)

FOREIGN PATENT DOCUMENTS

EP 0650707 A1 5/1995
EP 1779875 A1 5/2007
(Continued)

OTHER PUBLICATIONS

Balamurugan et al.; Development and spectral characterization of poly(methyl methacrylate)/hydroxyapatite composite for biomedical applications; Trends Biomater. Artif. Organs; 18(1); pp. 41-45; Jul. 2004.
(Continued)

*Primary Examiner* — Brian A Dukert
*Assistant Examiner* — Rebecca Lynee Zimmerman
(74) *Attorney, Agent, or Firm* — Clark & Elbing LLP

(57) ABSTRACT

The present disclosure pertains to ionic polymer compositions, including semi- and fully interpenetrating polymer networks, methods of making such ionic polymer compositions, articles made from such ionic polymer compositions, and methods of making such articles and packaging for such articles.

24 Claims, 4 Drawing Sheets

Related U.S. Application Data continuation-in-part of application No. 16/246,292, filed on Jan. 11, 2019, now abandoned.

(60) Provisional application No. 62/699,497, filed on Jul. 17, 2018.

(51) Int. Cl.

| | | |
|---|---|---|
| *A61F 2/30* | (2006.01) | |
| *A61F 2/32* | (2006.01) | |
| *A61F 2/38* | (2006.01) | |
| *A61F 2/40* | (2006.01) | |
| *A61F 2/42* | (2006.01) | |
| *A61F 2/44* | (2006.01) | |
| *A61L 27/26* | (2006.01) | |
| *A61L 27/18* | (2006.01) | |
| *A61F 2/00* | (2006.01) | |

(52) U.S. Cl.
CPC ............ *A61F 2/30756* (2013.01); *A61F 2/32* (2013.01); *A61F 2/3804* (2013.01); *A61F 2/389* (2013.01); *A61F 2/3872* (2013.01); *A61F 2/3877* (2013.01); *A61F 2/4081* (2013.01); *A61F 2/4202* (2013.01); *A61F 2/4225* (2013.01); *A61F 2/4241* (2013.01); *A61F 2/4261* (2013.01); *A61F 2/442* (2013.01); *A61F 2/4405* (2013.01); *A61L 27/18* (2013.01); *A61L 27/26* (2013.01); *A61L 27/48* (2013.01)

(58) Field of Classification Search
CPC .......... A61F 2/32; A61F 2/389; A61F 2/3099; A61F 2/4241; A61F 2/4405; A61F 2/4202; A61F 2/442; A61F 2/3877; A61F 2/3804; A61F 2/4261; A61L 27/34; A61L 27/26; A61L 27/48; A61L 27/18; A61L 2400/10; A61L 27/52; A61L 29/085; A61L 27/28; C08G 18/83; C08G 18/48; C08G 2270/00; C08J 3/246; C08F 285/00; C08F 283/006; C08F 8/36; C08L 2205/04; C08L 33/066; C08L 75/04; C08L 33/26; C08L 101/14
See application file for complete search history.

(56) References Cited

U.S. PATENT DOCUMENTS

| | | |
|---|---|---|
| 3,702,611 A | 11/1972 | Fishbein |
| 3,826,678 A | 7/1974 | Hoffman et al. |
| 3,833,404 A | 9/1974 | Sperling et al. |
| 3,939,049 A | 2/1976 | Ratner et al. |
| 4,035,848 A | 7/1977 | Wagner |
| 4,128,600 A | 12/1978 | Skinner et al. |
| 4,192,827 A | 3/1980 | Mueller et al. |
| 4,224,699 A | 9/1980 | Weber |
| 4,302,553 A | 11/1981 | Frisch et al. |
| 4,312,079 A | 1/1982 | Dorre et al. |
| 4,320,709 A | 3/1982 | Hladun |
| 4,391,797 A | 7/1983 | Folkman et al. |
| 4,423,099 A | 12/1983 | Mueller et al. |
| 4,439,583 A | 3/1984 | Gould et al. |
| 4,452,925 A | 6/1984 | Kuzma et al. |
| 4,468,499 A | 8/1984 | Siegfried et al. |
| 4,477,604 A | 10/1984 | Oechsle, III |
| 4,487,865 A | 12/1984 | Balazs et al. |
| 4,500,676 A | 2/1985 | Balazs et al. |
| 4,502,161 A | 3/1985 | Wall |
| 4,536,554 A | 8/1985 | Lim et al. |
| 4,575,539 A | 3/1986 | DeCrosta et al. |
| 4,621,637 A | 11/1986 | Fishbein |
| 4,657,941 A | 4/1987 | Blackwell et al. |
| 4,678,468 A | 7/1987 | Hiroyoshi |
| 4,680,336 A | 7/1987 | Larsen et al. |
| 4,693,715 A | 9/1987 | Abel, Jr. |
| 4,693,721 A | 9/1987 | Ducheyne |
| 4,816,495 A | 3/1989 | Blackwell et al. |
| 4,836,884 A | 6/1989 | McAuslan |
| 4,846,841 A | 7/1989 | Oh |
| 4,865,601 A | 9/1989 | Caldwell et al. |
| 4,913,144 A | 4/1990 | Del Medico |
| 4,931,287 A | 6/1990 | Bae et al. |
| 4,966,934 A | 10/1990 | Huang et al. |
| 4,973,493 A | 11/1990 | Guire |
| 4,978,352 A | 12/1990 | Fedorov et al. |
| 5,030,230 A | 7/1991 | White |
| 5,061,270 A | 10/1991 | Aboczky |
| 5,067,961 A | 11/1991 | Kelman et al. |
| 5,087,392 A | 2/1992 | Burke et al. |
| 5,091,205 A | 2/1992 | Fan |
| 5,094,876 A | 3/1992 | Goldberg et al. |
| 5,100,689 A | 3/1992 | Goldberg et al. |
| 5,112,350 A | 5/1992 | Civerchia et al. |
| 5,115,056 A | 5/1992 | Mueller et al. |
| 5,122,133 A | 6/1992 | Evans |
| 5,133,769 A | 7/1992 | Wagner et al. |
| 5,171,318 A | 12/1992 | Gibson et al. |
| 5,258,024 A | 11/1993 | Chavel et al. |
| 5,264,495 A | 11/1993 | Irie et al. |
| 5,276,070 A | 1/1994 | Arroyo |
| 5,282,851 A | 2/1994 | Jacob-Labarre |
| 5,290,548 A | 3/1994 | Goldberg et al. |
| 5,300,116 A | 4/1994 | Chirila et al. |
| 5,314,478 A | 5/1994 | Oka et al. |
| 5,374,515 A | 12/1994 | Parenteau et al. |
| 5,403,893 A | 4/1995 | Tanaka et al. |
| 5,476,515 A | 12/1995 | Kelman et al. |
| 5,554,665 A | 9/1996 | Tateosian et al. |
| 5,556,429 A | 9/1996 | Felt |
| 5,562,738 A | 10/1996 | Boyd et al. |
| 5,576,072 A | 11/1996 | Hostettler et al. |
| 5,587,406 A | 12/1996 | Yamamoto et al. |
| 5,589,563 A | 12/1996 | Ward et al. |
| 5,591,170 A | 1/1997 | Spievack et al. |
| 5,643,390 A | 7/1997 | Don et al. |
| 5,644,049 A | 7/1997 | Giusti et al. |
| 5,645,592 A | 7/1997 | Nicolais et al. |
| 5,656,210 A | 8/1997 | Hill et al. |
| 5,660,692 A | 8/1997 | Nesburn et al. |
| 5,674,942 A | 10/1997 | Hill et al. |
| 5,693,034 A | 12/1997 | Buscemi et al. |
| 5,716,633 A | 2/1998 | Civerchia |
| 5,733,289 A | 3/1998 | Seedhom et al. |
| 5,763,529 A | 6/1998 | Lucas |
| 5,770,669 A | 6/1998 | Robertson et al. |
| 5,800,412 A | 9/1998 | Zhang et al. |
| 5,824,079 A | 10/1998 | Siegler et al. |
| 5,834,532 A | 11/1998 | Yamamoto et al. |
| 5,836,313 A | 11/1998 | Perez et al. |
| 5,837,752 A | 11/1998 | Shastri et al. |
| 5,856,366 A | 1/1999 | Shiveley et al. |
| 5,904,927 A | 5/1999 | Amiji |
| 5,913,858 A | 6/1999 | Calandruccio et al. |
| 5,962,005 A | 10/1999 | Saga et al. |
| 5,976,648 A | 11/1999 | Li et al. |
| 6,001,894 A | 12/1999 | Ottersbach et al. |
| 6,005,160 A | 12/1999 | Hsiue et al. |
| 6,019,766 A | 2/2000 | Ling et al. |
| 6,027,742 A | 2/2000 | Lee et al. |
| 6,030,606 A | 2/2000 | Holmes |
| 6,031,017 A | 2/2000 | Waki et al. |
| 6,057,406 A | 5/2000 | Pojman et al. |
| 6,120,904 A | 9/2000 | Hostettler et al. |
| 6,160,084 A | 12/2000 | Langer et al. |
| 6,171,300 B1 | 1/2001 | Adams |
| 6,210,438 B1 | 4/2001 | Sheets, Jr. et al. |
| 6,214,044 B1 | 4/2001 | Silverstrini |
| 6,221,467 B1 | 4/2001 | Nazarova et al. |
| 6,224,893 B1 | 5/2001 | Langer et al. |
| 6,231,605 B1 | 5/2001 | Ku |
| 6,231,611 B1 | 5/2001 | Mosseri |

(56) References Cited

U.S. PATENT DOCUMENTS

| | | |
|---|---|---|
| 6,239,209 B1 | 5/2001 | Yang et al. |
| 6,251,965 B1 | 6/2001 | Wang et al. |
| 6,254,637 B1 | 7/2001 | Lee et al. |
| 6,264,695 B1 | 7/2001 | Stoy |
| 6,265,016 B1 | 7/2001 | Hostettler et al. |
| 6,281,271 B1 | 8/2001 | Rumphorst et al. |
| 6,306,177 B1 | 10/2001 | Felt et al. |
| 6,306,424 B1 | 10/2001 | Vyakarnam et al. |
| 6,331,578 B1 | 12/2001 | Turner et al. |
| 6,368,315 B1 | 4/2002 | Gillis et al. |
| 6,372,815 B1 | 4/2002 | Sulc et al. |
| 6,376,742 B1 | 4/2002 | Zdrahala et al. |
| 6,388,043 B1 | 5/2002 | Langer et al. |
| 6,391,055 B1 | 5/2002 | Ikada et al. |
| 6,428,576 B1 | 8/2002 | Haldimann |
| 6,429,256 B1 | 8/2002 | Vandevoorde et al. |
| 6,437,018 B1 | 8/2002 | Gertzman et al. |
| 6,440,444 B2 | 8/2002 | Boyce et al. |
| 6,479,565 B1 | 11/2002 | Stanley |
| 6,482,209 B1 | 11/2002 | Engh et al. |
| 6,494,917 B1 | 12/2002 | McKellop et al. |
| 6,509,098 B1 | 1/2003 | Merrill et al. |
| 6,585,771 B1 | 7/2003 | Buttermilch et al. |
| 6,610,067 B2 | 8/2003 | Tallarida et al. |
| 6,629,997 B2 | 10/2003 | Mansmann |
| 6,632,235 B2 | 10/2003 | Weikel et al. |
| 6,632,246 B1 | 10/2003 | Simon et al. |
| 6,645,715 B1 | 11/2003 | Griffith et al. |
| 6,652,587 B2 | 11/2003 | Felt et al. |
| 6,673,079 B1 | 1/2004 | Kane |
| 6,673,112 B2 | 1/2004 | Nigam |
| 6,679,917 B2 | 1/2004 | Ek |
| 6,689,165 B2 | 2/2004 | Jacob et al. |
| 6,726,322 B2 | 4/2004 | Andino et al. |
| 6,733,533 B1 | 5/2004 | Lozier |
| 6,740,087 B2 | 5/2004 | Knox |
| 6,755,865 B2 | 6/2004 | Tarabishy |
| 6,759,449 B2 | 7/2004 | Kimura et al. |
| 6,846,875 B2 | 1/2005 | Pennings et al. |
| 6,852,125 B2 | 2/2005 | Simon et al. |
| 6,866,936 B2 | 3/2005 | Opolski |
| 6,911,212 B2 | 6/2005 | Gertzman et al. |
| 6,918,914 B2 | 7/2005 | Bauer |
| 6,921,264 B2 | 7/2005 | Mayer et al. |
| 6,949,251 B2 | 9/2005 | Dalai et al. |
| RE38,839 E | 10/2005 | Magnante |
| 6,953,594 B2 | 10/2005 | Lee et al. |
| 6,955,540 B2 | 10/2005 | Mayer et al. |
| 6,960,617 B2 | 11/2005 | Omidian et al. |
| 6,976,997 B2 | 12/2005 | Noolandi et al. |
| 7,008,226 B2 | 3/2006 | Mayer et al. |
| 7,008,635 B1 | 3/2006 | Coury et al. |
| 7,018,460 B2 | 3/2006 | Xu et al. |
| 7,019,192 B2 | 3/2006 | Gertzman et al. |
| 7,029,479 B2 | 4/2006 | Tallarida et al. |
| 7,037,984 B2 | 5/2006 | Lendlein et al. |
| 7,049,351 B2 | 5/2006 | Phelan et al. |
| 7,066,958 B2 | 6/2006 | Ferree |
| 7,067,194 B2 | 6/2006 | Mao et al. |
| 7,083,650 B2 | 8/2006 | Moskowitz et al. |
| 7,094,286 B2 | 8/2006 | Liu |
| 7,105,026 B2 | 9/2006 | Johnson et al. |
| 7,160,305 B2 | 1/2007 | Schmieding |
| 7,163,541 B2 | 1/2007 | Ek |
| 7,176,247 B1 | 2/2007 | Walker, Jr. |
| 7,204,897 B2 | 4/2007 | Stoy et al. |
| 7,217,294 B2 | 5/2007 | Kusanagi et al. |
| 7,220,491 B2 | 5/2007 | Rouns et al. |
| 7,235,592 B2 | 6/2007 | Muratoglu et al. |
| 7,279,174 B2 | 10/2007 | Pacetti et al. |
| 7,279,507 B2 | 10/2007 | Hu et al. |
| 7,303,814 B2 | 12/2007 | Lamberti et al. |
| 7,335,205 B2 | 2/2008 | Aeschlimann et al. |
| 7,341,593 B2 | 3/2008 | Auxepaules et al. |
| 7,371,257 B2 | 5/2008 | Sahatjian et al. |
| 7,387,810 B2 | 6/2008 | Hossainy |
| 7,468,075 B2 | 12/2008 | Lang et al. |
| 7,476,398 B1 | 1/2009 | Doillon et al. |
| 7,563,483 B2 | 7/2009 | Hossainy et al. |
| 7,618,462 B2 | 11/2009 | Ek |
| 7,678,151 B2 | 3/2010 | Ek |
| 7,713,305 B2 | 5/2010 | Ek |
| 7,824,666 B2 | 11/2010 | Wolff et al. |
| 8,252,851 B2 | 8/2012 | Young et al. |
| 8,497,023 B2 | 7/2013 | Myung et al. |
| 8,679,190 B2 | 3/2014 | Myung et al. |
| 8,853,294 B2 | 10/2014 | Myung et al. |
| 8,883,915 B2 | 11/2014 | Myung et al. |
| 9,114,024 B2 | 8/2015 | Kourtis et al. |
| 9,387,082 B2 | 7/2016 | Myung et al. |
| 9,750,842 B2 | 9/2017 | Kourtis et al. |
| 10,457,803 B2 | 10/2019 | Myung et al. |
| 10,752,768 B2 | 8/2020 | Myung et al. |
| 10,792,392 B2 | 10/2020 | Kourtis et al. |
| 10,869,950 B2 | 12/2020 | Kourtis et al. |
| 2001/0029399 A1 | 10/2001 | Ku |
| 2001/0044026 A1 | 11/2001 | Vaghefi et al. |
| 2002/0022884 A1 | 2/2002 | Mansrnann |
| 2002/0055007 A1 | 5/2002 | Soane et al. |
| 2002/0082699 A1 | 6/2002 | Ward et al. |
| 2002/0091229 A1 | 7/2002 | Hubbell et al. |
| 2002/0173855 A1 | 11/2002 | Mansmann |
| 2002/0198280 A1 | 12/2002 | Baba et al. |
| 2003/0008396 A1 | 1/2003 | Ku |
| 2003/0022216 A1 | 1/2003 | Mao et al. |
| 2003/0028196 A1 | 2/2003 | Bonutti |
| 2003/0083389 A1 | 5/2003 | Kao et al. |
| 2003/0083433 A1 | 5/2003 | James et al. |
| 2003/0092777 A1 | 5/2003 | Leitner |
| 2003/0100666 A1 | 5/2003 | DeGroot et al. |
| 2003/0114936 A1 | 6/2003 | Sherwood et al. |
| 2003/0130741 A1 | 7/2003 | McMinn |
| 2003/0153981 A1 | 8/2003 | Wang et al. |
| 2003/0170308 A1 | 9/2003 | Cleary et al. |
| 2004/0028804 A1 | 2/2004 | Anderson et al. |
| 2004/0034437 A1 | 2/2004 | Schmieding |
| 2004/0044410 A1 | 3/2004 | Ferree et al. |
| 2004/0059425 A1 | 3/2004 | Schmieding |
| 2004/0116564 A1 | 6/2004 | Devlin et al. |
| 2004/0133275 A1 | 7/2004 | Mansmann |
| 2004/0134502 A1 | 7/2004 | Mizuno et al. |
| 2004/0138382 A1 | 7/2004 | Dous |
| 2004/0139382 A1 | 7/2004 | Kim |
| 2004/0147466 A1 | 7/2004 | Barman et al. |
| 2004/0147927 A1 | 7/2004 | Tsougarakis et al. |
| 2004/0153040 A1 | 8/2004 | Martineau et al. |
| 2004/0153079 A1 | 8/2004 | Tsougarakis et al. |
| 2004/0153163 A1 | 8/2004 | Posner |
| 2004/0167528 A1 | 8/2004 | Schantz |
| 2004/0171740 A1 | 9/2004 | Ruberti et al. |
| 2004/0199250 A1 | 10/2004 | Fell |
| 2004/0204760 A1 | 10/2004 | Fitz et al. |
| 2004/0214914 A1 | 10/2004 | Marmo |
| 2004/0230315 A1 | 11/2004 | Ek |
| 2004/0236424 A1 | 11/2004 | Berez et al. |
| 2004/0266941 A1 | 12/2004 | Houston et al. |
| 2004/0267363 A1 | 12/2004 | Fell et al. |
| 2005/0004306 A1 | 1/2005 | Lubnin et al. |
| 2005/0013793 A1 | 1/2005 | Beckman et al. |
| 2005/0027364 A1 | 2/2005 | Kim et al. |
| 2005/0033295 A1 | 2/2005 | Wisnewski |
| 2005/0038520 A1 | 2/2005 | Binette et al. |
| 2005/0049459 A1 | 3/2005 | Hern |
| 2005/0055044 A1 | 3/2005 | Kangas |
| 2005/0065616 A1 | 3/2005 | Ankorina-Stark et al. |
| 2005/0090612 A1 | 4/2005 | Soane et al. |
| 2005/0113836 A1 | 5/2005 | Lozier et al. |
| 2005/0113928 A1 | 5/2005 | Cragg et al. |
| 2005/0126680 A1 | 6/2005 | Aeschlimann et al. |
| 2005/0142162 A1 | 6/2005 | Hunter et al. |
| 2005/0147685 A1 | 7/2005 | Osada et al. |
| 2005/0171604 A1 | 8/2005 | Michalow |
| 2005/0186248 A1 | 8/2005 | Hossainy et al. |
| 2005/0187146 A1 | 8/2005 | Helmus et al. |

(56) References Cited

U.S. PATENT DOCUMENTS

| | | |
|---|---|---|
| 2005/0215660 A1 | 9/2005 | Tomikawa et al. |
| 2005/0218541 A1 | 10/2005 | Peng et al. |
| 2005/0228161 A1 | 10/2005 | Benz et al. |
| 2005/0251267 A1 | 11/2005 | Winterbottom et al. |
| 2005/0251268 A1 | 11/2005 | Truncale |
| 2005/0267482 A1 | 12/2005 | Hyde |
| 2005/0267584 A1 | 12/2005 | Burdulis et al. |
| 2005/0278025 A1 | 12/2005 | Ku et al. |
| 2005/0283255 A1 | 12/2005 | Geremakis et al. |
| 2005/0287187 A1 | 12/2005 | Mansmann |
| 2006/0008506 A1 | 1/2006 | Cipriano De Sousa et al. |
| 2006/0052878 A1 | 3/2006 | Schmieding |
| 2006/0083773 A1 | 4/2006 | Myung et al. |
| 2006/0093648 A1 | 5/2006 | Coury et al. |
| 2006/0105295 A1 | 5/2006 | Mayer et al. |
| 2006/0111726 A1 | 5/2006 | Felt et al. |
| 2006/0122543 A1 | 6/2006 | Mayer et al. |
| 2006/0134186 A1 | 6/2006 | Carlton et al. |
| 2006/0142406 A1 | 6/2006 | Schmitt et al. |
| 2006/0148985 A1 | 7/2006 | Karthauser |
| 2006/0188487 A1 | 8/2006 | Thomas et al. |
| 2006/0188940 A1 | 8/2006 | Cima et al. |
| 2006/0193899 A1 | 8/2006 | Sawhney |
| 2006/0224244 A1 | 10/2006 | Thomas et al. |
| 2006/0233855 A1 | 10/2006 | Seliktar et al. |
| 2006/0235517 A1 | 10/2006 | Hodorek |
| 2006/0235539 A1 | 10/2006 | Blunn et al. |
| 2006/0235542 A1 | 10/2006 | Hodorek et al. |
| 2006/0240478 A1 | 10/2006 | Nishimi et al. |
| 2006/0241629 A1 | 10/2006 | Krebs et al. |
| 2006/0241759 A1 | 10/2006 | Trieu |
| 2006/0246241 A1 | 11/2006 | Kruger et al. |
| 2006/0282169 A1 | 12/2006 | Felt et al. |
| 2006/0287721 A1 | 12/2006 | Myung et al. |
| 2006/0287730 A1 | 12/2006 | Segal et al. |
| 2007/0014828 A1 | 1/2007 | Fitzhugh et al. |
| 2007/0016211 A1 | 1/2007 | Botimer |
| 2007/0048382 A1 | 3/2007 | Meyer et al. |
| 2007/0067032 A1 | 3/2007 | Felt et al. |
| 2007/0068816 A1 | 3/2007 | Solomon et al. |
| 2007/0078388 A1 | 4/2007 | Kangas |
| 2007/0078518 A1 | 4/2007 | Lavi |
| 2007/0083266 A1 | 4/2007 | Lang |
| 2007/0087031 A1 | 4/2007 | Ashman et al. |
| 2007/0088444 A1 | 4/2007 | Hodorek et al. |
| 2007/0098675 A1 | 5/2007 | Elisseeff et al. |
| 2007/0099840 A1 | 5/2007 | Ulijn et al. |
| 2007/0100457 A1 | 5/2007 | Hyde |
| 2007/0118218 A1 | 5/2007 | Hooper |
| 2007/0126982 A1 | 6/2007 | Myung et al. |
| 2007/0134291 A1 | 6/2007 | Ting et al. |
| 2007/0135922 A1 | 6/2007 | Trieu |
| 2007/0141108 A1 | 6/2007 | Thomas et al. |
| 2007/0142914 A1 | 6/2007 | Jones et al. |
| 2007/0149441 A1 | 6/2007 | Aeschlimann et al. |
| 2007/0167541 A1 | 7/2007 | Ruberti et al. |
| 2007/0179605 A1 | 8/2007 | Myung et al. |
| 2007/0179607 A1 | 8/2007 | Hodorek et al. |
| 2007/0179622 A1 | 8/2007 | Denoziere et al. |
| 2007/0191963 A1 | 8/2007 | Winterbottom et al. |
| 2007/0198022 A1 | 8/2007 | Lang et al. |
| 2007/0202148 A1 | 8/2007 | Ringeisen et al. |
| 2007/0219640 A1 | 9/2007 | Steinberg |
| 2007/0224238 A1 | 9/2007 | Mansmann et al. |
| 2007/0225823 A1 | 9/2007 | Hawkins et al. |
| 2007/0233240 A1 | 10/2007 | Frank et al. |
| 2007/0233269 A1 | 10/2007 | Steines et al. |
| 2007/0265704 A1 | 11/2007 | Mayer et al. |
| 2007/0270783 A1 | 11/2007 | Zumsteg et al. |
| 2007/0276394 A1 | 11/2007 | Johnson et al. |
| 2008/0058954 A1 | 3/2008 | Trieu |
| 2008/0070086 A1 | 3/2008 | Fukuchi et al. |
| 2008/0077249 A1 | 3/2008 | Gradel |
| 2008/0103505 A1 | 5/2008 | Fransen |
| 2008/0124376 A1 | 5/2008 | Pruitt et al. |
| 2008/0139694 A1 | 6/2008 | Ratcliffe |
| 2008/0182919 A1 | 7/2008 | Saimi et al. |
| 2008/0241214 A1 | 10/2008 | Myung et al. |
| 2008/0269370 A1 | 10/2008 | Myung et al. |
| 2008/0317818 A1 | 12/2008 | Griffith et al. |
| 2009/0035344 A1 | 2/2009 | Thomas et al. |
| 2009/0062408 A1 | 3/2009 | Liu et al. |
| 2009/0062423 A1 | 3/2009 | Betz et al. |
| 2009/0088846 A1 | 4/2009 | Myung et al. |
| 2009/0142508 A1 | 6/2009 | Lai et al. |
| 2009/0163860 A1 | 6/2009 | Patrick et al. |
| 2009/0176891 A1 | 7/2009 | Chogle et al. |
| 2009/0209966 A1 | 8/2009 | Chandler |
| 2009/0221730 A1 | 9/2009 | Kowalski et al. |
| 2009/0233887 A1 | 9/2009 | Shalaby et al. |
| 2009/0234044 A1 | 9/2009 | Rheinberger et al. |
| 2009/0240337 A1 | 9/2009 | Myung et al. |
| 2009/0281545 A1 | 11/2009 | Stubbs |
| 2009/0312807 A1 | 12/2009 | Boudreault et al. |
| 2010/0010114 A1 | 1/2010 | Myung et al. |
| 2010/0032090 A1 | 2/2010 | Myung et al. |
| 2010/0056646 A1 | 3/2010 | Shalaby et al. |
| 2010/0125341 A1 | 5/2010 | Frauens |
| 2011/0152868 A1 | 6/2011 | Kourtis et al. |
| 2011/0184423 A1 | 7/2011 | Rushton et al. |
| 2011/0237705 A1 | 9/2011 | Leonard et al. |
| 2012/0045651 A1 | 2/2012 | Myung et al. |
| 2012/0116531 A1 | 5/2012 | Forsell |
| 2012/0209396 A1 | 8/2012 | Myung et al. |
| 2012/0232657 A1 | 9/2012 | Myung et al. |
| 2012/0277807 A1 | 11/2012 | Myung et al. |
| 2012/0308508 A1 | 12/2012 | Saunders et al. |
| 2013/0096691 A1 | 4/2013 | Myung et al. |
| 2013/0103157 A1 | 4/2013 | Kourtis et al. |
| 2013/0131741 A1 | 5/2013 | Kourtis et al. |
| 2013/0138210 A1 | 5/2013 | Myung et al. |
| 2013/0138211 A1 | 5/2013 | Myung et al. |
| 2013/0217829 A1 | 8/2013 | Myung et al. |
| 2014/0172098 A1 | 6/2014 | Myung et al. |
| 2015/0025161 A1 | 1/2015 | Myung et al. |
| 2015/0272599 A1 | 10/2015 | Kourtis et al. |
| 2015/0284654 A1 | 10/2015 | Myung et al. |
| 2016/0346089 A1 | 12/2016 | Myung et al. |
| 2017/0107370 A1 | 4/2017 | Myung et al. |
| 2017/0327624 A1 | 11/2017 | Kourtis et al. |
| 2017/0348011 A1 | 12/2017 | Kourtis et al. |
| 2018/0236136 A1 | 8/2018 | Kourtis et al. |
| 2019/0218386 A1 | 7/2019 | Kourtis et al. |
| 2019/0224367 A1 | 7/2019 | Kourtis et al. |
| 2020/0046880 A1 | 2/2020 | Kourtis et al. |

FOREIGN PATENT DOCUMENTS

| | | |
|---|---|---|
| EP | 2268331 A2 | 1/2011 |
| EP | 2626090 A2 | 8/2013 |
| GB | 2372707 A | 9/2002 |
| JP | H06-287443 A | 10/1994 |
| JP | H10-500038 A | 1/1996 |
| JP | H09-077809 A | 3/1997 |
| JP | 3176176 B2 | 6/2001 |
| JP | 2002514233 A | 5/2002 |
| JP | 2002518564 A | 6/2002 |
| JP | 2002518565 A | 6/2002 |
| JP | 2003171475 A | 6/2003 |
| JP | 2004512079 A | 4/2004 |
| JP | 2004515311 A | 5/2004 |
| JP | 2005305162 A | 11/2005 |
| JP | 2006517842 A | 8/2006 |
| JP | 2007501674 A | 2/2007 |
| WO | WO-94/01468 A1 | 1/1994 |
| WO | WO-95/30388 A1 | 11/1995 |
| WO | WO-98/06768 A1 | 2/1998 |
| WO | WO-99/45978 A1 | 9/1999 |
| WO | WO-99/67311 A1 | 12/1999 |
| WO | WO-99/67312 A1 | 12/1999 |
| WO | WO-00/02937 A1 | 1/2000 |
| WO | WO-00/043050 A1 | 7/2000 |
| WO | WO-02/026848 A2 | 4/2002 |
| WO | WO-03/009337 A2 | 1/2003 |

(56) References Cited

FOREIGN PATENT DOCUMENTS

| WO | WO-2004/032767 A1 | 4/2004 |
|---|---|---|
| WO | WO-2004/055057 A1 | 7/2004 |
| WO | WO-2004/073563 A2 | 9/2004 |
| WO | WO-2004/091685 A2 | 10/2004 |
| WO | WO-2007/067697 A2 | 6/2007 |
| WO | WO-2007/068625 A1 | 6/2007 |
| WO | WO-2007/112305 A2 | 10/2007 |
| WO | WO-2008/100617 A1 | 8/2008 |
| WO | WO-2009/071937 A1 | 6/2009 |
| WO | WO-2010/037685 A1 | 4/2010 |
| WO | WO-2010/059495 A2 | 5/2010 |
| WO | WO-2012/096997 A2 | 7/2012 |
| WO | WO-2015/023569 A1 | 2/2015 |
| WO | WO-2017/027590 A1 | 2/2017 |

OTHER PUBLICATIONS

Barszczewska-Rybarek, Izabela M.; Quantitative determination of degree of conversion in photocured poly (urethane-dimethacrylate)s by Fourier transform infrared spectroscopy; Journal of Applied Polymer Science; vol. 123; issue 3; pp. 1604-1611; Feb. 5, 2012.
Bobyn et al., The optimum pore size for the fixation of porous-surfaced metal implants by the ingrowth of bone. Clin Orthop Relat Res, Jul./Aug. 1980(150): p. 263-70.
Borden et al.; The sintered microsphere matrix for bone tissue engineering: In vitro osteoconductivity studies; J. Biomed. Mat. Res.; 61(3); pp. 421-429; Sep. 2002.
Brodbeck et al., Biomaterial adherent macrophage apoptosis is increased by hydrophilic and anionic substrates in vivo. Proc Natl Acad Sci U S A, Aug. 6, 2002. 99(16): p. 10287-92.
Brown et al.; Solvent/Non-solvent sintering: A novel route to create porous microsphere scaffolds for tissue regeneration; J. Biomed. Mat. Res. (Part B: Applied Biomaterials); 86B(2); pp. 396-406; Aug. 2008.
Causton et al.; Dental materials: 1981 literature review Part 1; Journal of Dentistry; vol. 12; Issue 1; pp. 1R28; Mar. 1984.
Charnley, J.; Anchorage of the femoral head prosthesis to the shaft of the femur; J Bone Joint Surg Br.; 42-B:28-30; Feb. 1960.
Chen et al.; Mechanical Properties of Polyepichlorohydrin Polyurethane/Poly(methyl methacrylate) IPNs; Chinese J Appl Chem; 12(4):66-69; Aug. 1995 (wEngAbs).
Christenson et al., "Antioxidant inhibition of poly(carbonate urethane) in vivo biodegradation," J Biomed Mater Res A. 76(3): 480-490 (2006).
Covert et al.; Friction characteristics of a potential articular cartilage biomaterial. Wear, Aug. 2003. 255: p. 1064-1068.
Depuy Orthopaedics; Bone Cement Time Setting Chart; product file; date of publication unknown; available to applicants at least as of Jul. 2012.
Dror et al.; Gradient interpenetrating polymer networks. I. Poly(ether urethane) and polyacrylamide IPN; J of Applied Polymer Science; 26; pp. 1741-1757; Jun. 1981.
Elbert; Liquid-liquid two phase systems for the production of porous hydrogels and hydrogel microspheres for biomedical applications: A tutorial review; Acta Biomater; 7(1); pp. 31-56; Jan. 31, 2011.
Elmer's Products Inc.; Material Safety Data Sheet; "Elmer's Nano Glue"; Jun. 13, 2007.
Elsabee et al.; Gradient interpenetrating polymer networks. II. Polyacrylamide gradients in poly(ether urethane); J of Applied Polymer Science; 28(7); pp. 2151-2166; Jun. 1983.
Esstech, Inc.; Urethane Dimethacrylate (product specification); 1 pg.; Note: this document was available to applicant(s) at least as of (Apr. 8, 2015).
Evans et al.; The use of corneal organ culture in biocompatibility studies; Biomaterials; vol. 23; pp. 1359-1367; Mar. 2002.
Forsell; U.S. Appl. No. 61/229,735 entitled "Hip Joint Method," filed Jul. 30, 2009.

Frank, Curt; Structure-property relationships for hydrogels with applications to biomedical devices; Presentation at American Chemical Society Mtg; San Francisco, CA; Sep. 11, 2006.
Gao et al.; Grafting of hydrophilic monomers onto polyurethane membranes by solution or pre-absorbing methods for acceleration of cell compatibility; Chinese Journal of Polymer Science; vol. 19; No. 5; pp. 493-498; Oct. 20, 2001.
Gong et al.; Double-network hydrogels with extremely high mechanical strength; Adv. Mater.; vol. 15; No. 14; pp. 1155-1158; Jul. 17, 2003.
Gorna et al., "Biodegradable porous polyurethane scaffolds for tissue repair and regeneration," J Biomed Mater Res A. 79(1):128-38 (2006).
Gorna et al.; Preparation, degradation, and calcification of biodegradable polyurethane foams for bone graft substitutes; J Biomed Mater Res A. 67(3): 813-827 (2003).
Goswami et al.; Engineering properties of novolac resin-PMMA {Poly(methyl methacrylate)} IPN system; Journal of Applied Science; 93(6); pp. 2764-2774; Jul. 16, 2004.
Guelcher et al.; Synthesis and in vitro biocornpatibility of injectable polyurethane foam scaffolds; Tissue Engineering; 12(5); pp. 1247-1259; May 2006.
Guelcher et al.; Synthesis of biocompatible segmented polyurethanes from aliphatic diisocyanates and diurea diol chain extenders; Acta biomaterialia; 1(4); pp. 471-484; Jul. 2005.
Gunatillake et al.; Designing biostable polyurethane elastomers for biomedical implants; Aust. J. Chem.; vol. 56; pp. 545-557; Jun. 2003.
Hern et al.; Incorporation of adhesion peptides into nonadhesive hydrogels useful for tissue resurfacing; J. Biomed. Materials Research; vol. 39; No. 1; pp. 266-276; Feb. 1998.
Hsieh et al.; Compatibility and Morphology in Polyurethane and Polystyrene Ionomeric Interpenetrating Polymer Networks; Polymer Journal; 21(1); pp. 1-10; Jan. 15, 1989.
International Search Report for International Application No. PCT/US08/01642, dated May 16, 2008 (1 page).
International Search Report for International Application No. PCT/US16/46350, dated Oct. 14, 2016 (3 pages).
International Search Report for International Application No. PCT/US19/42193, dated Sep. 27, 2019 (3 pages).
International Search Report for International Application No. PCT/US2008/004976, dated Oct. 15, 2009 (4 pages).
Ithaca College Gross Anatomy; Joints of the Back; ; 4 pgs. (downloaded Dec. 1, 2013 from http://www.ithaca.edu/faculty/lahr/LE2000/Back/Jointpage.htm).
Iwasaki et al., Hydrogel-like elastic membrane consisting of semi-interpenetrating polymer networks based on a phosphorylcholine polymer and a segmented polyurethane; J. Polym. Sci Part A: Polym Chem; 41; pp. 68-75; Jan. 2003.
Jones et al.; Sequential Polyurethane-Poly(Methylmethacrylate) Interpenetrating Polymer Networks as Ureteral Biomaterials: Mechanical Properties and Comparative Resistance to Urinary Encrustation; J Mater Sci Mater Med; 8(11):713-717; Nov. 1997.
Kagata et al., "Friction of Gels. 6. Effects of Sliding Velocity and Viscoelastic Responses of the Network," J Phys Chem B. 106(18):4596-601 (2002).
Kaneko et al., "Mechanically Strong Hydrogels with Ultra-Low Frictional Coefficients," Advanced Materials. 17(5):535-8 (2005).
Kanie et al.; Flexural properties of ethyl or methyl methacrylate-UDMA blend polymers; Dent Mater J; 29(5); pp. 575-581; Oct. 2010.
Khan et al., Analysis and evaluation of a biomedical polycarbonate urethane tested in an in vitro study and an ovine arthroplasty model. Part I: materials selection and evaluation. Biomaterials, Feb. 2005. 26(6): p. 621-31.
Kim et al.; Adhesion and growth of endothelial cell on amphiphilic PU/PS. IPN surface: effect of amphiphilic balance and immobilized collagen; Journal of Biomedical Materials Research; 62(4); pp. 613-621; Sep. 6, 2002.
Kim et al.; Electrical/pH Responsive Properties of Poly(2-acrylamido-2-methylpropane sulfonic acid)/Hyaluronic Acid Hydrogels; Journal of Applied Polymer Science; vol. 92; issue 3; pp. 1731-1736; May 2004.

(56) References Cited

OTHER PUBLICATIONS

Kim et al.; Electrochemical behavior of an interpenetrating polymer network hydrogel composed of poly (propylene glycol) and poly(acrylic acid); Journal of Applied Polymer Science; vol. 89; pp. 2301-2305; Aug. 2003.
Kim et al.; Water sorption of ploy(propylene glycol)/poly(acrylic acid) interpenetrating polymer network hydrogels; Reactive & Functional Polymers; vol. 55; pp. 69-73; Feb. 2003.
Kourtis et al., U.S. Appl. No. 13/573,788, entitled "Polymeric adhesive for anchoring compliant materials to another surface," filed Oct. 3, 2012 (103 pages).
Kourtis et al., U.S. Appl. No. 13/683,731, entitled "Systems, Devices, and Methods for Anchoring Orthopaedic Implants to Bone," filed Nov. 21, 2012 (130 pages).
Kourtis et al.; U.S. Appl. No. 15/442,413, entitled "Method, device, and system for shaving and shaping of a joint," filed Feb. 24, 2017 (69 pages).
Kourtis et al.; U.S. Appl. No. 15/668,547, entitled "Polymeric adhesive for achoring compliant materials to another surface," filed Aug. 3, 2017 (109 pages).
Kourtis et al.; U.S. Appl. No. 15/752,168, entitled "Interpenetrating polymer networks," filed Feb. 12, 2018 (109 pages).
Kourtis et al.; U.S. Appl. No. 12/973,829, entitled "Method, device, and system for shaving and shaping of a joint," filed Dec. 20, 2010 (69 pages).
Kwong et al., "A comparison of the shrinkage of commercial bone cements when mixed under vacuum" J Bone Joint Surg Br. 88 (1 ):120-2 (2006).
Lam et al.; Update on Ureteral Stents; Urology; 64:9-15; Jul. 2004.
Lamba et al.; Polyurethanes in Biomedical Applications; CRC Press; pp. 11, 14, 16, 18-20, 57-59, 73, 79 & 104; Nov. 1997.
Lee et al.; Interpenetrating polymer network hydrogels based on poly (ethylene glycol) macromer and chitosan; Carbohydrate Polymer; vol. 41; No. 2; pp. 197-205; Feb. 2000.
Lewis G., "Properties of acrylic bone cement: state of the art review," J Biomed Mater Res. 38(2):155-82 (1997).
Lipatov et al.; Gradient interpenetrating polymer networks; Journal of Materials Science; 30(4); pp. 1095-1104; Feb. 1995.
Lu et al.; Release behavior of high molecular weight solutes from poly(ethylene glycol)-based degradable networks; Macromolecules; vol. 33(7); pp. 2509-2515; Mar. 2000.
Maroudas et al.; Permeability of articular cartilage; Nature; vol. 219(5160); pp. 1260-1261; Sep. 21, 1968.
Matinlinna et al., "Isocyanato- and Methacryloxysilanes Promote Bis-GMA Adhesion to Titanium," J Dent Res. 84(4):360-364 (2005).
MIT.edu; Material Modulus Properties; 2pgs.; Feb. 8, 2007 (downloaded Nov. 27, 2013 from http://web.archive.org/web/*/http://web.mit.edu/course/3/3.11/www/modules- /props.pdf).
Morgan et al., "Dependence of yield strain of human trabecular bone on anatomic site," J Biomech. 34(5):569-77 (2001).
Mow et al., Basic Orthopaedic Biomechanics and Mechano-Biology, Lippincot Williams and Wilkins, 3rd Edition, Apr. 2005, pp. 459-461.
Myung et al.; Biomimetic strain hardening in interpenetrating polymer network hydrogels; Polymer,; vol. 48; No. 18; pp. 5376-5387; Jun. 2007.
Myung et al.; U.S. Appl. No. 12/409,359, entitled "Methods, devices and compositions for adhering hydrated polymer implants to bone," filed Mar. 23, 2009 (45 pages).
Myung et al.; U.S. Appl. No. 12/499,041, entitled "Hydrophilic Interpenetrating Polymer Networks Derived From Hydrophobic Polymers," filed Jul. 7, 2009 (95 pages).
Myung et al.; U.S. Appl. No. 12/536,233, entitled "Polyurethane-grafted hydrogels," filed Aug. 5, 2009 (51 pages).
Myung et al.; U.S. Appl. No. 13/347,647, entitled "Orthopedic implants having gradient polymer alloys," filed Jan. 10, 2012 (144 pages).
Myung et al.; U.S. Appl. No. 13/418,294, entitled "Hydrogel Anthroplasty Device," filed Mar. 12, 2012 (99 pages).

Myung et al.; U.S. Appl. No. 13/542,464, entitled "Methods, Devices and Compositions for Adhering Hydrated Polymer Implants to Bone," filed Jul. 5, 2012 (48 pages.).
Myung et al.; U.S. Appl. No. 13/748,573, entitled "Hydrophilic Interpenetrating Polymer Networks Derived From Hydrophobic Polymers," filed Jan. 23, 2013 (99 pages).
Myung et al.; U.S. Appl. No. 13/748,576, entitled "Hydrophilic Interpenetrating Polymer Networks Derived From Hydrophobic Polymers," filed Jan. 23, 2013 (103 pages).
Myung et al.; U.S. Appl. No. 13/816,537, entitled "Hydrophobic and Hydrophilic Interpenetrating Polymer Networks Derived From Hydrophobic Polymers and Methods of Preparing the Same," filed Apr. 24, 2013 (153 pages).
Myung et al.; U.S. Appl. No. 13/905,028, entitled "Polyurethane-grafted hydrogels," filed May 29, 2013 (58 pages).
Myung, David; Structure, properties, and medical device applications of mechanically enhanced, biometric hydrogel alloys; Doctoral Thesis; Stanford University; Dec. 2007.
Nanci et al., "Chemical modification of titanium surfaces for covalent attachment of biological molecules," J Biomed Mater Res. 40(2):324-35 (1998) (13 pages).
Neurosurgical.com; Spinal Anatomy: The Regions of the Spine; 5pgs. (downloaded Dec. 1, 2013 http://www.neurosurgical.com/neuro_medical_info/spinal_anatomy.htm).
Ohman et al.; Mechanical testing of cancellous bone from the femoral head: experimental errors due to off-axis measurements; J Biomech.; 40(11):2426-33; (year of publication is sufficiently earlier than the effective U.S. filed and any foreignpriority date) 2007.
Orr et al., "Shrinkage stresses in bone cement," Biomaterials. 24(17):2933-40 (2003).
Pan et al., "A study on the friction properties of poly (vinyl alcohol) hydrogel as articular cartiliage against titanium alloy," Wear. 262(7-8):1021-5 (2007).
Park et al.; Synthesis of PVA/PVP hydrogels having two-layer by radiation and their physical properties; Radiation Physics and Chemistry; 67(3-4); pp. 361-365; Jun. 2003.
Puska et al.; Exothermal Characteristics and Release of Residual Monomers from Fiber-reinforced Oligomer-modified Acrylic Bone Cement; J Biomat App; 20:51-64; Jul. 2005.
Realdictionary; Definition of Implant; 4pgs. (downloaded Dec. 1, 2013 from www.realdictionary.com/?q=implant).
Revzin et al., "Fabrication of Poly(ethylene glycol) Hydrogel Microstructures Using Photolithography," Langmuir. 17(18):5440-7 (2001).
Saito et al.; Preparation and properties of transparent cellulose hydrogels; J. Applied Polymer Science; 90(11); pp. 3020-3025; Dec. 2003.
Scholes et al.; Compliant layer acetabular cups: friction testing of a range of materials and designs for a new generation of prosthesis that mimics the natural joint; Proc. IMechE; vol. 220(5); Part H; J. Engineering in Medicine; pp. 583-596, Jul. 2006.
Shalaby; U.S. Appl. No. 61/069,046 entitled "Hydroswellable, segmented, aliphatic polyurethanes and polyurethane ureas," filed Mar. 12, 2008.
Sigma-Aldrich; Methyl Methacrylate (product specification); 1 pg.; Note: this document was available to applicant(s) at least as of (Jun. 19, 2014).
Simon et al., "Study of two Grafting Methods for Obtaining a 3-Aminopropyltriethoxysilane Monolayer on Silica Surface," J Colloid Interface Sci. 251(2):278-83 (2002).
Spector et al.; Porous polymers for biological fixation. Clin Orthop Relat Res, Oct. 1988 (235): p. 207-19.
Stammen et al., Mechanical properties of a novel PVA hydrogel in shear and unconfined compression. Biomaterials, Apr. 2001. 22(8): p. 799-806.
Stryker Orthopaedics; SimplexTM P Bone Cement; Product Literature LSB Rev. 3, Mar. 2006.
Swieszkowski et al., "An elastic material for cartilage replacement in an arthritic shoulder joint," Biomaterials. 27(8):1534-41 (2006).
Tanaka et al.; Polymer properties on resins composed of UDMA and methacrylates with the carboxyl group; Dental Materials Journal; 20(3); pp. 206-215; Sep. 2001.
Tariq et al.; (Abstract) Sodium benzoate attenuates iminodipropionitrile-induced behavioral syndrome in rats. Behav pharmacol; Dec. 2004.

(56) References Cited

OTHER PUBLICATIONS

Tawfik, Dan; Amidation of carboxyl groups; The Protein Protocols Handbook, 2nd Ed.; Humana Press; pp. 477-478; Feb. 2002.
The Engineering Toolbox; Polyurethane insulation: {http://www.engineeringtoolbox.com/polyurethane-insulation-k-values-d_117-4.html} pp. 1-3; printed Oct. 21, 2011.
The Engineering Toolbox;Thermal conductivity of some common materials and gases: {http://www.engineeringtoolbox.com/thrmal-conductivity-d_429.html} pp. 1-2; printed Oct. 21, 2011.
The Gorilla Glue Company; Material Safety Data Sheet; "New Fast Cure-Dries White Gorilla Glue.RTM."; Jan. 30, 2007.
The Gorilla Glue Company; Material Safety Data Sheet; "New Stronger-Faster Gorilla Glue.RTM."; Jan. 26, 2007.
Van Landuyt et al.; Reinforcement of Osteosynthesis Screws with Brushite Cement; Bone; 25(2)(Suppl 1 ):95S-98S; Aug. 1999.
Wittemann et al.; Adsorption of proteins on spherical polyelectrolyte brushes in aqueous solution; Phys. Chem. Chem. Phys., Mar. 2003, vol. 5(8), pp. 1671-1677.
Wright et al., Wear studies on prosthetic materials using the pin-on-disc machine. Biomaterials, vol. 3, Issue 1, Jan. 1982, pp. 41R48.
Written Opinion for International Application No. PCT/US08/01642, dated May 16, 2008 (5 pages).
Written Opinion for International Application No. PCT/US16/46350, dated Oct. 14, 2016 (8 pages).
Written Opinion for International Application No. PCT/US19/42193, dated Sep. 27, 2019 (6 pages).
Written Opinion for International Application No. PCT/US2008/004976, dated Oct. 15, 2009 (6 pages).
Xiao et al., "Covalent Attachment of Cell-Adhesive, (Arg-Gly-Asp)-Containing Peptides to Titanium Surfaces," Langmuir.14(19):5507-16 (1998).
Yang et al.; Preparation of poly(acrylic acid) modified polyurethane membrane for biomaterial by UV radiation without degassing; J. Biomed. Mater. Res.; vol. 45(2); pp. 133-139; May 1999.
Yim et al., Biocompatibility of poly(ethylene glycol)/poly(acrylic acid)interpenetrating polymer network hydrogel particles inRAW 264.7 macrophage and MG-63 osteoblast cell lines. Journal of Biomedical Materials Research, 91A(3); pp. 894-902; Dec. 1, 2009.
Zhu et al.; (Abstract) Promoting the cytocompatibility of polyurethane scaffolds via surface photo-grafting polymerization of acrylamide; J. Mater. Sci. Mater. Med.; vol. 15; No. 3; pp. 283-289; Mar. 2004.

IONIC POLYMER COMPOSITIONS

CROSS REFERENCE TO RELATED APPLICATIONS

This application is a continuation of U.S. application Ser. No. 16/514,279, filed Jul. 17, 2019, which is a continuation-in-part of U.S. application Ser. No. 16/246,292, filed Jan. 11, 2019 entitled "Ionic Polymer Compositions" and claims the benefit of U.S. Application Ser. No. 62/699,497, filed Jul. 17, 2018 and entitled "Ionic Polymer Compositions". The disclosure of each of the preceding applications is hereby incorporated by reference in its entirety.

FIELD OF THE DISCLOSURE

The present disclosure pertains to ionic polymer compositions, including semi- and fully interpenetrating polymer networks, methods of making such ionic polymer compositions, articles made from such ionic polymer compositions, and methods of making such articles and packaging for such articles.

BACKGROUND OF THE DISCLOSURE

Fully interpenetrating polymer networks (IPN's) and semi-interpenetrating polymer networks ("semi-IPN's") have been created from a variety of starting materials and have been used for a variety of applications. IPN's and semi-IPN's can combine the beneficial properties of each of the polymers from which they are made.

IPN's and semi-IPN's are described for biomedical applications, for example, in U.S. Patent Publ. No. 2009/0008846. U.S. Patent Publ. No. 2013/0096691, U.S. Patent Publ. No. 2017/0107370, U.S. Patent Publ. No. 2012/0045651, U.S. Patent Publ. No. 2012/0209396, U.S. Patent Publ. No. 2017/0327624, U.S. Patent Publ. No. 2013/0131741, and WO 2017/027590.

SUMMARY OF THE DISCLOSURE

For purposes of this application, "carboxylic acid groups" may refer to both non-ionized (protonated) and ionized (carboxylate) forms of these groups. For purposes of this application, "sulfonic acid groups" may refer to both non-ionized (protonated) and ionized (sulfonate) forms of these groups.

For purposes of this application, an "interpenetrating polymer network" or "IPN" is a material comprising two or more polymer networks which are at least partially interlaced on a molecular scale, but not covalently bonded to each other, and cannot be separated unless chemical bonds are broken. A "semi-interpenetrating polymer network" or "semi-IPN" is a material comprising one or more polymer networks and one or more linear or branched polymers characterized by the penetration on a molecular scale of at least one of the networks by at least some of the linear or branched macromolecules. Semi-interpenetrating polymer networks are distinguished from interpenetrating polymer networks because the constituent linear or branched polymers can, in principle, be separated from the constituent polymer network(s) without breaking chemical bonds; they are polymer blends.

A "polymer" is a substance comprising macromolecules, including homopolymers (a polymer derived from one species of monomer) and copolymers (a polymer derived from more than one species of monomer). A "hydrophobic polymer" is a pre-formed polymer network having at least one of the following two properties: (1) a surface water contact angle of at least 45° and (2) exhibits water absorption of 2.5% or less after 24 hours at room temperature according to ASTM test standard D570. A "hydrophilic polymer" is a polymer network having a surface water contact angle less than 45° and exhibits water absorption of more than 2.5% after 24 hours at room temperature according to ASTM test standard D570. An "ionic polymer" is defined as a polymer comprised of macromolecules containing ionic monomers (e.g., monomers with carboxylate group, sulfonate groups, or both), ionizable monomers (e.g., monomers with protonated carboxyl groups, protonated sulfonate groups, or both), or both ionic monomers and ionizable monomers, typically, at least 2% by weight ionic or ionizable monomers (or both), irrespective of their nature and location. A "thermoset polymer" is one that doesn't melt when heated, unlike a thermoplastic polymer. Thermoset polymers "set" into a given shape when first made and afterwards do not flow or melt, but rather decompose upon heating and are often highly crosslinked and/or covalently crosslinked. A "thermoplastic polymer" is one which melts or flows when heated, unlike thermoset polymers. Thermoplastic polymers are usually not covalently crosslinked. "Phase separation" is defined as the conversion of a single-phase system into a multi-phase system; especially the separation of two immiscible blocks of a block co-polymer into two phases, with the possibility of a small interphase in which a small degree of mixing occurs.

In certain aspects, the present disclosure pertains to ionic polymers that comprise a combination of carboxylic acid groups and sulfonic acid groups. In certain of these aspects, the present disclosure pertains to ionic polymers that comprise a combination of underivatized groups and sulfonic-acid-derivatized groups.

In certain aspects, the present disclosure pertains to ionic polymers that comprise a combination of underivatized carboxylic acid groups and sulfonic-acid-derivatized groups, including amino-sulfonic-acid-derivatized carboxylic acid groups.

In certain aspects, sulfonic-acid-derivatized groups are only found at the surface of the ionic polymer. In certain aspects, sulfonic-acid-derivatized groups may extend from a surface of the ionic polymer and into a bulk of the ionic polymer by a distance of at least 10 microns, at least 50 microns, at least 100 microns, at least 250 microns, at least 500 microns, at least 1000 microns, at least 2500 microns, or at least 5000 microns, at least 10000 microns or more, for example, extending into the bulk of the ionic polymer by a distance ranging from 0 microns to 10 microns to 25 microns to 50 microns to 100 microns to 250 microns to 500 microns to 1000 microns to 2500 microns to 5000 microns to 10000 microns or more.

In certain aspects, at least 1%, at least 5%, at least 10%, at least 15%, at least 20%, at least 25%, at least 50%, at least 75%, at least 80%, at least 85%, at least 90%, at least 95% or all of the thickness of the ionic polymer has sulfonic-acid derivatized groups.

In certain aspects, the sulfonic-acid-derivatized groups extend from a surface of the ionic polymer into a bulk of the ionic polymer and are present in detectable amounts up to a distance from the surface of at least 250 microns, at least 500 microns, at least 1000 microns, at least 2500 microns, at least 5000 microns, or at least 10000 microns, or more, for example, being present in detectable amounts at a distance from the surface ranging from 250 microns to 500 microns to 1000 microns to 2500 microns to 5000 microns to 10000 microns or more.

In certain of these aspects, a concentration of sulfonic-acid-derivatized groups in the ionic polymer falls to no less than 50% of a concentration of sulfonic-acid-derivatized groups at the surface up to a distance from the surface of at least 100 microns, at least 250 microns, at least 500 microns, at least 1000 microns, at least 2500 microns, at least 5000 microns, at least 10000 microns, or more.

In certain aspects, at a depth of 100 microns, a concentration of sulfonic-acid-derivatized groups in the ionic polymer may range from 0% to 5% to 10% to 25% to 50% to 75% to 90% to 95% to 100% of a surface concentration of the sulfonic-acid-derivatized groups.

In certain aspects, ionic polymers as described herein, including any of the ionic polymers described above, may have a thickness ranging from about 2 mm to 3 mm to 4 mm to 5 mm to 7.5 mm to 10 mm or more.

In certain aspects, the present disclosure pertains to interpenetrating polymer networks and semi-interpenetrating polymer networks that comprise ionic polymers as described herein, including any of the ionic polymers described above. Such interpenetrating polymer networks and semi-interpenetrating polymer networks may, for example, have a thickness ranging from about 2 mm to 3 mm to 4 mm to 5 mm to 7.5 mm to 10 mm or more.

In certain aspects, the present disclosure pertains to methods of forming ionic polymers as described herein and interpenetrating and semi-interpenetrating polymer networks that comprise ionic polymers as described herein.

In certain aspects, the present disclosure pertains to implants, including orthopedic implants, that are formed from ionic polymers as described herein and from interpenetrating and semi-interpenetrating polymer networks that comprise ionic polymers as described herein.

In certain aspects, the present disclosure pertains to packaged products that contain implants, including orthopedic implants, that are formed from ionic polymers as described herein and interpenetrating and semi-interpenetrating polymer networks that comprise ionic polymers as described herein.

In various embodiments, the implants are at least partially immersed in a divalent-cation-containing solution comprising water and one or more divalent metal cations. The divalent-cation-containing solution may be, for example, a simulated body fluid that contains physiologic levels of ions found in the body fluids such as synovial fluid or blood serum or cerebrospinal fluid. In certain embodiments, the divalent-cation-containing solution may comprise 0.1 to 5 mM total divalent metal cations. The concentration of total divalent cations in a solution is the combined concentration of all divalent cations in the solution. (For example, if one liter of solution contains 0.5 millimole of calcium cations. 0.5 millimole of magnesium cations, and no other divalent cations, then that solution contains 1.0 mM total divalent cations.) In certain embodiments, the divalent-cation-containing solution may comprise calcium ions, magnesium ions or a combination of calcium ions and magnesium ions. For instance, the divalent-cation-containing solution may comprise 0.5 to 5.0 mM calcium ions, typically 0.5 to 2.0 mM calcium ions, more typically 0.8 to 1.6 mM calcium ions, and in some embodiments 1.1 to 1.3 mM calcium ions, among other possibilities and/or the divalent-cation-containing solution may comprise 0.2 to 1.5 mM magnesium ions, typically 0.3 to 1.0 mM magnesium ions, and in some embodiments, 0.5 to 0.7 mM magnesium ions, among other possibilities. In certain embodiments, the divalent-cation-containing solution may further comprise monovalent metal ions selected from sodium ions, potassium ions, or a combination of sodium and potassium ions, in which case the divalent-cation-containing solution may contain 0 to 300 mM total monovalent metal cations, among other possibilities. In various embodiments, the ionic polymer comprises carboxylic acid groups, sulfonic acid groups, or a combination of carboxylic acid groups and sulfonic acid groups as described elsewhere herein.

In various embodiments, the implants comprise an interpenetrating or semi-interpenetrating polymer network that comprises a first polymeric network comprising a first polymer and a second polymeric network comprising an ionic polymer as described elsewhere herein.

In various embodiments, the implants may be selected from a hip implant, a knee implant, a shoulder implant, hand implant, a toe implant, or anywhere else in the body where desired to replace cartilage, as described elsewhere herein. In some embodiments, the implant is configured to repair or replace cartilage in a joint in the body, such as a knee joint, a condyle, a patella, a tibial plateau, ankle joint, an elbow joint, a shoulder joint, a finger joint, a thumb joint, a glenoid, a hip joint, an intervertebral disc, an intervertebral facet joint, a labrum, a meniscus, a metacarpal joint, a metatarsal joint, a toe joint, a temporomandibular joint, or a wrist joint, and any portion thereof.

In certain aspects, the present disclosure pertains to implants, including orthopedic implants such as those described elsewhere herein, which maintain dimension and mechanical properties under divalent conditions.

In certain aspects, the present disclosure pertains to implants, including orthopedic implants such as those described elsewhere herein, which maintain water content (i.e., within a range of ±5 wt %, preferably ±2 wt %, more preferably ±1 wt %), throughout a physiologic range of divalent ion concentrations found in living organisms, including synovial fluid of living organisms, particularly mammals, more particularly human beings.

In certain aspects, the present disclosure pertains to implants, including orthopedic implants such as those described elsewhere herein, which demonstrate an absolute % weight change per mM change in total divalent cation concentration of less than 10%, less than 5%, less than 3%, less than 2%, or even less than 1% (ideally demonstrating no measurable weight change), for example, demonstrating such properties over a total divalent cation concentration range of from about 0.1 mM to about 5 mM, including a total divalent cation concentration ranging from hypo-physiological divalent cation levels of 1.4 mM (0.96 mM $Ca^{2+}$, 0.48 mM $Mg^{2+}$) to hyper-physiological divalent cation levels of 2.2 mM (1.44 mM $Ca^{2+}$, 0.72 mM $Mg^{2+}$).

In certain aspects, the present disclosure pertains to implants, including orthopedic implants such as those described elsewhere herein, which maintain a coefficient of friction of less than 0.1, preferably less than 0.075, more preferably less than 0.05, over a total divalent cation concentration range of about 0.1 mM to about 5 mM, including over a physiologic total divalent cation concentration range of about 1.4 mM (0.96 mM $Ca^{2+}$, 0.48 mM $Mg^{2+}$ to about 2.2 mM (1.44 mM $Ca^{2+}$, 0.72 mM $Mg^{2+}$).

The present disclosure includes processes for modifying common commercially available hydrophobic thermoset or thermoplastic polymers, such as polyurethanes or acrylonitrile butadiene styrene (ABS) to provide novel materials with new properties, such as increased strength, lubricity, electrical conductivity and wear-resistance. Various hydrophobic thermoset or thermoplastic polymers are described below. The disclosure also includes IPN and semi-IPN compositions as well as articles made from such compositions and methods of using such articles. The IPN and semi-IPN compositions of this disclosure may attain one or more of the following characteristics: high tensile and compressive strength; low coefficient of friction; high water content and swellability; high permeability; biocompatibility; and biostability.

Applications of the present disclosure include the creation of hydrophilic, lubricious articles and coatings to reduce the static and dynamic coefficient of friction between two bearing surfaces and to reduce biofilm formation and/or barnacle formation in marine vessels, other water crafts or waterborne objects, or pipes. Furthermore, applications of the present disclosure include electrochemical applications that require conduction of electrical current, or permeability of ions such as proton exchange membranes, fuel cells, filtration devices, and ion-exchange membranes. In addition, the present disclosure can be used as a method for making bearings and moving parts for applications such as engines, pistons, or other machines or machine parts. The present disclosure can also be used in numerous biomedical applications including cartilage substitutes, orthopedic joint replacement and resurfacing devices or components thereof, intervertebral discs, stents, vascular or urinary catheters, condoms, heart valves, vascular grafts, and both short-term and long-term implants in other areas of the body, such as skin, brain, spine, the gastro-intestinal system, the larynx, and soft tissues in general. In addition, the present disclosure can be used as a component of various surgical tools and instruments. In various applications drugs can be incorporated into the materials of the present disclosure for localized drug delivery, including drug delivery vehicles in which a therapeutic agent is released from a polymer matrix.

As previously noted, in certain aspects, the present disclosure pertains to ionic polymers that comprise a combination of underivatized carboxylic acid groups and sulfonic-acid-derivatized groups, including amino-sulfonic-acid-derivatized carboxylic acid groups, and methods of forming the same.

Sulfonic acid functional groups may be incorporated into an already formed solid article (i.e., in a solid state, including porous and non-porous articles) comprising a precursor polymer that comprises carboxylic acid groups. In some embodiments, the sulfonic acid functional groups may be incorporated into an already formed IPN or semi-IPN (including a gradient IPN or semi-IPN) that comprises carboxylic acid groups. The general principle is to replace the carboxylic acid groups present on a poly(carboxylic acid), for example, on a poly(acrylic acid) or poly(methacrylic acid) in an IPN with sulfonic acid-containing functional groups, among other possibilities. In some embodiments, methods are provided which comprise reacting (a) a solid article comprising a precursor polymer that comprises carboxylic acid groups with (b) a sulfonic-acid-containing compound (e.g., by reacting the carboxylic acid groups of the solid article with an amino sulfonic acid compound such that an amide bond is formed between the carboxylic acid groups of the precursor polymer and the amine groups of the amino sulfonic acid compound).

In certain embodiments, a hydrophilic-hydrophobic IPN as presented in US2013/0138210, hereby incorporated by reference, which contains carboxylic acid groups (e.g., carboxylate ionic groups) can be sulfonated by means of amidation using an amine containing sulfonic acid (i.e., an amino sulfonic acid). An amide (peptide) bond is formed between carboxylates of the IPN and the amine in the sulfonic acid.

In some embodiments, the amino sulfonic acid compound is a compound of the formula $(H_2N)_xR(SO_3H)_y$ or a salt thereof, where R is an organic moiety, where x is a positive integer, and wherein y is a positive integer. In certain embodiments, x may range from 1 to 10, typically, 1 to 5 (i.e., x may be 1, 2, 3, 4 or 5) and y may range from 1 to 10, typically, 1 to 5 (i.e., y may be 1, 2, 3, 4 or 5). In some embodiments, the compound of the formula $(H_2N)_xR(SO_3H)_y$ has a hydrodynamic radius that allows the diffusion of the molecule within the IPN. R may be, for example, hydrocarbon moiety, for example, a including linear, branched or cyclic hydrocarbon moiety, or a hydrocarbon moiety having a combination of two or more of linear, branched and cyclic hydrocarbon substituents. The hydrocarbon moiety may be, for example, C1-C12 hydrocarbon or a polymeric moiety including polymeric/oligomeric containing heteroatoms. In certain embodiments, the hydrocarbon moiety may be selected from an alkane moiety, an alkene moiety, an alkyne moiety, an aromatic moiety, or a hydrocarbon moiety having a combination of two or more of alkane, alkene, alkyne or aromatic substituents. In certain embodiments, the amino sulfonic acid may be selected from taurine,

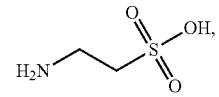

and taurine derivatives, including 1-substituted, 2-substituted, 1,1-disubstituted, 2,2-disubstituted, and 1,2-disubstituted taurines, such as 1-hydrocarbon-substituted, 2-hydrocarbon-substituted, 1,1-hydrocarbon-disubstituted, 2,2-hydrocarbon-disubstituted, and 1,2-hydrocarbon-disubstituted taurines, where the substituted hydrocarbons may be selected, for example, from the hydrocarbon moieties described above. In other embodiments, the amino sulfonic acid compound is one that results in the formation of 2-acrylamido-2-methyl propane sulfonic acid or acrylamido ethane sulfonic acid.

In various embodiments, the methods comprise contacting the solid article comprising the precursor polymer having carboxylic acid groups with the sulfonic-acid-containing compound such that the sulfonic-acid-containing compound (e.g., an amino sulfonic acid compound) is diffused into the solid article.

In various embodiments, the methods further comprise contacting the solid article comprising the precursor polymer having carboxylic acid groups with a coupling reagent such that the coupling reagent is diffused into the solid article, thereby activating reactive groups (e.g., carboxylic acid groups) within the solid article and promoting reaction with the sulfonic-acid-containing compound (e.g., by promoting the formation of amide bonds between carboxylic acid groups of a precursor polymer within the solid article and amine groups of the amino sulfonic acid. In these embodiments, the coupling reagent may be diffused into the solid article before the sulfonic-acid-containing compound is diffused into the solid article, the coupling reagent may be diffused into the solid article after the sulfonic-acid-containing compound is diffused into the solid article, or the coupling reagent and the sulfonic-acid-containing compound may be diffused into the solid article simultaneously.

Examples of coupling reagents include triazine-based coupling reagents, as well as carbodiimide, phosphonium and aminium salts, organophosphorus reagents, and fluoroformamidinium coupling reagents. In particular embodiments, the coupling reagent may be a carbodiimide coupling reagent selected from 1-Ethyl-3-(3-dimethylaminopropyl) carbodiimide (EDC). 1,3-bis(2,2-dimethyl-1,3-dioxolan-4-ylmethyl)carbodiimide (BDDC), and 1-cyclohexyl-3-[2-morpholinoethyl]carbodiimide. In particular embodiments, the coupling reagent may be a triazine-based coupling agent selected from derivatives of 2,4,6-trichloro-1,3,5-triazine including 2,4-dichloro-6-methoxy-1,3,5-triazine (DCMT), 2-chloro-4,6,-dimethoxy-1,3,5-triazine (CDMT), its derivative with N-methylmorpholine (NMM), 4-(4,6-dimethoxy-1,3,5-triazin-2-yl)-4-methylmorpholinium chloride (DMTMM). As discussed in more detail below, applicant has found that, by employing suitable coupling agents, including triazine-based coupling reagents, under suitable conditions, sulfonic-acid-derivatized groups may be incorporated into the solid article comprising the precursor polymer having carboxylic acid groups at depths that range from a few microns to hundreds of microns or throughout the whole depth of the material. In various embodiments, the depth to which the sulfonic-acid-derivatized groups extend can be increased by repeating the reaction with the sulfonic-acid-containing compound.

The precursor polymer having carboxylic acid groups may be, for example, a homopolymer or copolymer (e.g., an alternating copolymer, random copolymer, gradient copolymer, block copolymer, etc.). The precursor polymer having carboxylic acid groups may be selected, for example, from polymers comprising one or more monomers selected from acrylic acid, methacrylic acid, crotonic acid, linolenic acid, maleic acid, and fumaric acid, among others.

In various embodiments, the solid article may comprise an interpenetrating or semi-interpenetrating polymer network that comprises a first polymeric network comprising a first polymer and a second polymeric network comprising the precursor polymer having carboxylic acid groups. The first polymer may be, for example, a hydrophobic polymer. The first polymer may be, for example, a thermoplastic or thermoset polymer. In various embodiments described herein, the first polymer may be a hydrophobic thermoplastic or thermoset polymer. In certain beneficial embodiments, the first polymer may be hydrophobic thermoplastic polyurethane, such as a hydrophobic thermoplastic polyether urethane, among others.

In some embodiments, the present disclosure pertains to an IPN or semi-IPN (also referred to herein for convenience as a "mixed anion IPN or semi-IPN") that comprises (a) a first polymeric network comprising a first polymer and (b) a second polymeric network comprising a crosslinked ionic polymer that comprises sulfonic-acid-derivatized groups. For example, the first polymer may comprise a first polymer as described elsewhere herein, and the ionic polymer may comprise a combination of underivatized carboxylic acid groups and sulfonic-acid-derivatized carboxylic acid groups. As another example, the first polymer may comprise a first polymer as described elsewhere herein, and the ionic polymer may comprise a combination of underivatized carboxylic acid groups, sulfonic-acid-derivatized carboxylic acid groups, and uncharged groups. As another example, the first polymer may comprise a first polymer as described elsewhere herein, and the ionic polymer may comprise a combination of sulfonic-acid-derivatized carboxylic acid groups, optional uncharged groups, and negligible or no underivatized carboxylic acid groups (e.g., due to the conversion of all or essentially all of the underivatized carboxylic acid groups).

In some embodiments, the first polymer is a hydrophobic thermoset or thermoplastic polymer and the mixed anion IPN or semi-IPN exhibits a lower coefficient of friction than the hydrophobic thermoset or thermoplastic polymer. In some embodiments, the mixed anion IPN or semi-IPN is more water-swellable, exhibits higher resistance to creep, and/or exhibits a higher conductivity and permeability than the hydrophobic thermoset or thermoplastic polymer. Some embodiments of the composition also include an anti-oxidation agent.

In some embodiments, the mixed anion IPN or semi-IPN is formed by diffusing monomers comprising carboxylic-acid-group-containing monomers into the first polymer (e.g., a hydrophobic thermoset or thermoplastic polymer) and polymerizing the monomers to form a precursor polymer comprising carboxylic acid groups. Subsequently, a sulfonic-acid-containing compound is diffused into the IPN or semi-IPN and a portion of the carboxylic acid groups in the precursor polymer is derivatized as described elsewhere herein, thereby providing an ionic polymer that comprises a combination of underivatized carboxylic acid groups and sulfonic-acid-derivatized carboxylic acid groups. The sulfonic-acid-containing compound may be, for example, an amino sulfonic acid of the formula $(I_2N)_xR(SO_3H)_y$, as described above.

In particular embodiments, the mixed anion IPN or semi-IPN may comprise between 15 and 40% w/w, even more particularly, between 25 and 30 of the ionic polymer.

In particular embodiments, between 10 and 40% mol %, even more particularly, between 21 and 31 mol % of a total quantity of underivatized carboxylic acid groups and sulfonic-acid-derivatized carboxylic acid groups in the mixed anion IPN or semi-IPN (referred to herein as "the total quantity") are sulfonic-acid-derivatized carboxylic acid groups and between 90 and 60 mol %, even more particularly between 79 and 69 mol % of the total quantity are underivatized carboxylic acid groups.

In some embodiments, the mixed anion IPN or semi-IPN also includes water. In certain cases, the water which may form a hydration gradient from a first portion of the composition to a second portion of the composition. An electrolyte may be dissolved in the water.

In various embodiments, the hydrophobic thermoset or thermoplastic polymer may be physically entangled or chemically crosslinked with the ionic polymer (i.e., the polymer comprising a combination of underivatized carboxylic acid groups and sulfonic-acid-derivatized carboxylic acid groups).

In some embodiments, the hydrophobic thermoset or thermoplastic polymer has ordered and disordered domains, and the ionic polymer may be disposed in the disordered domains.

In various embodiments the hydrophobic thermoset or thermoplastic polymer may be selected from the group consisting of polymethyl methacrylate, polydimethylsiloxane, acrylonitrile butadiene styrene, polymethylmethacrylate, and polyurethanes including polyether urethanes, polycarbonate urethanes, silicone polyether urethanes, and silicone polycarbonate urethanes.

In various embodiments, the precursor polymer comprising underivatized carboxylic acid groups and the ionic polymer comprising a combination of underivatized carboxylic acid groups and sulfonic-acid-derivatized carboxylic acid groups may be formed from one or more monomers selected from acrylic acid, methacrylic acid, crotonic acid, linolenic acid, maleic acid, and fumaric acid.

In various embodiments, an article formed from the ionic polymer comprising a combination of underivatized carboxylic acid groups and sulfonic-acid-derivatized carboxylic acid groups (e.g., amino-sulfonic-acid-derivatized carboxylic acid groups) is provided in which a concentration of the underivatized carboxylic acid groups and a concentration of the sulfonic-acid-derivatized carboxylic acid groups are substantially constant.

In various embodiments, an article formed from the ionic polymer comprising a combination of underivatized carboxylic acid groups and sulfonic-acid-derivatized carboxylic acid groups is provided in which a concentration of the underivatized carboxylic acid groups and/or a concentration of the sulfonic-acid-derivatized carboxylic acid groups is relatively constant throughout the article. For example, (a) an article may be provided in which a concentration of the underivatized carboxylic acid groups varies by most+/−10%, at most+/−5%, at most+/−2%, at most+/−1%, or even less, throughout the article and/or (b) an article may be provided in which a concentration of the sulfonic-acid-derivatized carboxylic acid groups varies by at most+/−10%, at most +/−5% Mat most+/−2%, at most+/−1%, or even less, throughout the article.

In various embodiments, an article formed from the ionic polymer comprising a combination of underivatized carboxylic acid groups and sulfonic-acid-derivatized carboxylic acid groups is provided in which a concentration of the underivatized carboxylic acid groups and/or a concentration of the sulfonic-acid-derivatized carboxylic acid groups varies substantially within the article. For example, an article may be provided in which (a) a concentration of the underivatized carboxylic acid groups within the article varies by at least +/−10%, at least +/−25%, at least +/−50%, at least +/−100%, at least +/−250%, at least +/−500%, at least +/−1000%, or more, between two points (i.e., two locations) within the article (e.g., between a one surface of the article and an opposing surface of the article, between an exterior of the article and an interior of the article, etc.) and/or (b) a concentration of the sulfonic-acid-derivatized carboxylic acid groups within the article varies by at least +/−10%, at least +/−25%, at least +/−50%, at least +/−100%, at least +/−250%, at least +/−500%, at least +/−100%, or more, between two points within the article (e.g., between a one surface of the article and an opposing surface of the article, between an exterior of the article and an interior of the article, etc.).

In various embodiments, an article formed from the ionic polymer comprising a combination of underivatized carboxylic acid groups and sulfonic-acid-derivatized carboxylic acid groups is provided in which there is a gradient in a concentration of the underivatized carboxylic acid groups and/or a gradient in a concentration of the sulfonic-acid-derivatized carboxylic acid groups. In some of these embodiments, the gradients may approximate the shape of a step function. For example, (a) an article may be provided in which a concentration of the underivatized carboxylic acid groups decreases with increasing distance from at least one outer surface of the article (e.g., decreasing by at least 10%, at least 25%, at least 50%, at least 75%, at least 90% up to 100% from the at least one outer surface of the article to an interior point (i.e., an interior location) within the article, also referred to herein as a point in the bulk of the article), (b) an article may be provided in which a concentration of the underivatized carboxylic acid groups increases with increasing distance from at least one outer surface of the article (e.g., increasing by at least 10%, at least 20%, at least 50%, at least 100%, at least 200%, at least 500%, at least 1000% or more from the at least one outer surface of the article to an interior point within the article), (c) an article may be provided in which a concentration of the sulfonic-acid-derivatized carboxylic acid groups within the ionic polymer decreases with increasing distance from at least on outer surface of the article (e.g., decreasing by at least 10%, at least 25%, at least 50%, at least 75%, at least 90% up to 100% from the at least one outer surface of the article to an interior point within the article), or (d) an article may be provided in which a concentration of the sulfonic-acid-derivatized carboxylic acid groups within the ionic polymer increases with increasing distance from at least on outer surface of the article (e.g., increasing by at least 10%, at least 20%, at least 50%, at least 100%, at least 200%, at least 500%, at least 1000% or more from the at least one outer surface of the article to an interior point within the article).

Absolute values of the molar ratio of the sulfonic-acid-derivatized carboxylic acid groups to the underivatized carboxylic acid groups at various points within the article may vary widely. The molar ratio of the sulfonic-acid-derivatized carboxylic acid groups to the underivatized carboxylic acid groups at a given point within the article may range from 100000:1 or more (including infinity, where 100% of the underivatized carboxylic acid groups are converted to sulfonic-acid-derivatized carboxylic acid groups) to 1:100 or less. For example, the molar ratio of the sulfonic-acid-derivatized carboxylic acid groups to the underivatized carboxylic acid groups at a given point within the article may range from 1000:1 to 50000:1 to 25000:1 to 100:1 to 5000:1 to 2500:1 to 1000:1 to 500:1 to 250:1 to 100:1 to 50:1 to 25:1 to 10:1 to 5:1 to 2.5:1 to 1:1 to 1:2.5 to 1:5 to 1:10 to 1:25 to 1:50 to 1:100) (i.e., ranging between any two of the preceding ratios).

Articles formed from the ionic polymer comprising a combination of underivatized carboxylic acid groups and sulfonic-acid-derivatized carboxylic acid groups may be provided wherein a molar ratio of the sulfonic-acid-derivatized carboxylic acid groups to the underivatized carboxylic acid groups is relatively constant throughout the article, or where a molar ratio of the sulfonic-acid-derivatized carboxylic acid groups to the underivatized carboxylic acid groups varies substantially within the article.

In embodiments where an article formed from the ionic polymer comprising a combination of underivatized carboxylic acid groups and sulfonic-acid-derivatized carboxylic acid groups is provided in which a molar ratio of the sulfonic-acid-derivatized carboxylic acid groups to the underivatized carboxylic acid groups within the article is relatively constant within the article the molar ratio may vary, for example, by at most+/−10%, at most+/−5%, at most+/−2%, at most+/−1%, or less, throughout the article.

In embodiments where an article formed from the ionic polymer comprising a combination of underivatized carboxylic acid groups and sulfonic-acid-derivatized carboxylic acid groups is provided in which a molar ratio of the sulfonic-acid-derivatized carboxylic acid groups to the underivatized carboxylic acid groups varies substantially within the article, there may be a variation in the molar ratio of the sulfonic-acid-derivatized carboxylic acid groups to the underivatized carboxylic acid groups of at least +/−10%, at least +/−25%, at least +1-50%, at least +/−100% at least +/−250%, at least +/−500%, at least +/−1000%, or more, between two points within the article (e.g., between a one surface of the article and an opposing surface of the article, between an exterior of the article and an interior of the article, etc.). In some embodiments, there may be a gradient in a molar ratio of the sulfonic-acid-derivatized carboxylic acid groups to the underivatized carboxylic acid groups within the article. For example, a molar ratio of the sulfonic-acid-derivatized carboxylic acid groups to the underivatized carboxylic acid groups may increase between one surface of the article and an opposing surface of the article or increase between an exterior surface of the article and an interior of the article. As another example, a molar ratio of the sulfonic-acid-derivatized carboxylic acid groups to the underivatized carboxylic acid groups may decrease between one surface of the article and an opposing surface of the article or decrease between an exterior surface of the article and an interior of the article.

In this regard, as noted above, the ionic polymer may be formed from an article comprising a precursor polymer that comprises underivatized carboxylic acid groups by diffusing a coupling reagent into the article and by diffusing a sulfonic-acid-containing compound into the article, wherein the coupling reagent may be diffused into the solid article before, after, or at the same time as, the sulfonic-acid-containing compound is diffused into the article. Consequently, concentration gradients for the underivatized carboxylic acid groups and for the sulfonic-acid-derivatized carboxylic acid groups within the resulting article may be independently adjusted and thus are commonly different from one another. For example, in various embodiments, a molar ratio of the concentration of the sulfonic-acid-derivatized carboxylic acid groups relative to the underivatized carboxylic acid groups may decrease with increasing distance from an outer surface of the article into the interior of the article.

A concentration gradient in sulfonic-acid-derivatized carboxylic acid groups and/or underivatized carboxylic acid groups in an article may, for example, provide a stiffness and/or hydration gradient within the article.

Some embodiments include a second hydrophobic thermoset or thermoplastic polymer which may be disposed in a layer separate from the first hydrophobic thermoset or thermoplastic polymer or may be diffused throughout the first hydrophobic thermoset or thermoplastic polymer.

In some embodiments, a layer of another material is deposited onto one surface of an article formed from the ionic polymer comprising a combination of underivatized carboxylic acid groups and sulfonic-acid-derivatized carboxylic acid groups during the manufacturing process as a coating. This material may be added, for example, to the non-hydrated surface of an article containing a gradient ionic polymer. The material may be a bonding agent or version of the bonding agent and is physically, chemically, or physicochemically adhered to the surface of the article formed from the ionic polymer, for example, the non-hydrated surface of the article containing the gradient ionic polymer. By having this material coating disposed on this surface, the strength of a bonding agent applied at a later time is enhanced. In some embodiments, this strength is enhanced because the coating material and the bonding agent are compositionally the same or similar. In other embodiments, the coating is the same material as that at the surface of the article. In some embodiments, the coating is a different material—at least in part—as the that at the surface of the article. The coating may be a polymer, co-polymer, or polymer blend, and in one embodiment, is a co-polymer of polymethylmethacrylate and urethane dimethacrylate. The coating may be a thin coating that is applied during an implant manufacturing process, and may be applied by a variety of means including but not limited to spin-coating, spray-coating, vapor-deposition, solution casting, painting, and lithography. In other embodiments, the surface of one side of the article is roughened by application of an organic solvent and/or mechanical means such as but not limited to sanding, sand-blasting, lithography, and/or impression-molding. In some embodiments, the coating is applied to the roughened surface. In other embodiments, the roughened surface exists without any additional coating.

Another aspect of the disclosure provides a process for producing a water-swellable IPN or semi-IPN from an hydrophobic thermoset or thermoplastic polymer including the following steps: placing a liquid comprising one or more carboxylic-acid-group-containing monomers (e.g., made up of pure monomers or monomers in solution) in contact with a solid form of the hydrophobic thermoset or thermoplastic polymer; diffusing the one or more carboxylic-acid-group-containing monomers into the thermoset or thermoplastic polymer; and polymerizing the one or more carboxylic-acid-group-containing monomers to form an ionic polymer comprising carboxylic acid groups inside the thermoset or thermoplastic polymer, thereby forming a precursor IPN or semi-IPN having carboxylic acid groups.

Subsequently, a liquid comprising one or more amino sulfonic acid compounds is contacted with the precursor IPN or semi-IPN having carboxylic acid groups such that the one or more amino sulfonic acid compounds diffuse into the precursor IPN or semi-IPN, under conditions such that the one or more amino sulfonic acid compounds react with carboxylic acid groups of the precursor IPN or semi-IPN to form amide bonds, resulting in a mixed anion IPN or semi-IPN that contains underivatized carboxylic acid groups and amino-sulfonic-acid-derivatized carboxylic acid groups. For example, an amino sulfonic acid of the formula the amino sulfonic acid is a compound of the formula $(H_2N)_xR(SO_3H)_y$ as discussed above, may be reacted with carboxylic acid groups, —COOH, within the precursor IPN or semi-IPN, to form —$CONH(H_2N)_{x-1}R(SO_3H)_y$ groups. In various embodiments, a liquid comprising coupling reagent is contacted with the precursor IPN or semi-IPN prior to, at the same time, or after contact with the liquid containing the one or more amino sulfonic acid compounds, such that the coupling reagent reacts with the carboxylic acid groups, thereby activating the carboxylic acid groups for amide bond formation with the one or more amino sulfonic acid compounds.

Some embodiments include the step of swelling the mixed anion IPN or semi-IPN with water. e.g., to form a hydration gradient from a first portion of the composition to a second portion of the composition. The method may also include the step of swelling the mixed anion IPN or semi-IPN with an electrolyte solution.

In some embodiments, the hydrophobic thermoset or thermoplastic polymer is selected from polyurethane, polymethyl methacrylate, polydimethylsiloxane, acrylonitrile butadiene styrene and polymethylmethacrylate, polyether urethane, polycarbonate urethane, silicone polyether urethane, and silicone polycarbonate urethanes among others. The carboxylic-acid-group-containing monomer solution used to form the ionic polymer comprising carboxylic acid groups inside the thermoset or thermoplastic polymer may be selected from acrylic acid monomers, methacrylic acid monomers, crotonic acid monomers, linolenic acid monomers, maleic acid monomers, and fumaric acid monomers, among other monomers comprising carboxylic acid groups.

Some embodiments include the step of changing the precursor IPN or semi-IPN or mixed anion IPN or semi-IPN from a first shape to a second shape, such as by heating the precursor IPN or semi-IPN or mixed anion IPN or semi-IPN.

Yet another aspect of the disclosure provides a medical implant (e.g., an orthopedic implant, etc.) including a water-swellable mixed anion IPN or semi-IPN including a hydrophobic thermoset or thermoplastic polymer and an ionic polymer comprising a combination of underivatized carboxylic acid groups and sulfonic-acid-derivatized carboxylic acid groups, the implant having a bone contacting surface shaped to conform to a bone surface. Some embodiments also include a fluid capsule disposed in an interior region of the implant. Some embodiments have an insertion portion adapted to be inserted into a bone and a joint interface portion adapted to be disposed within a joint space, such as bone screws, sutures, or staples engaged with the mixed anion IPN or semi-IPN and adapted to engage the bone to attach the mixed anion IPN or semi-IPN to the bone and/or a stein extending from the bone contact surface and adapted to be inserted into the bone. The medical implant may also be incorporated as a bearing component of another device, such as a metal-based prosthesis.

The medical implant may also include a bonding agent adapted to attach the medical implant to a bone, such as a bone ingrowth surface formed on the bone contact surface. In some embodiments, the ionic polymer comprising a combination of underivatized carboxylic acid groups and sulfonic-acid-derivatized carboxylic acid groups forms a concentration gradient from a first portion of the implant to a second portion of the implant. Some embodiments have a second hydrophobic thermoset or thermoplastic polymer adjacent to the first hydrophobic thermoset or thermoplastic polymer, the ionic polymer comprising a combination of underivatized carboxylic acid groups and sulfonic-acid-derivatized carboxylic acid groups interpenetrating at least the first hydrophobic thermoset or thermoplastic polymer.

In some embodiments, implants formed from ionic polymers as described herein, including implants containing water-swellable mixed anion IPNs or semi-IPNs as described herein, may have properties mimicking stiffness and lubricity properties of natural cartilage. In some embodiments, implants formed from ionic polymers as described herein, including implants containing water-swellable mixed anion IPNs or semi-IPNs as described herein, may be adapted and configured to replace cartilage in a joint. For example, the implants may have a shape selected from the group consisting of a cap, a cup, a plug, a mushroom, a cylinder, a stem, and a patch. The implant may be adapted to repair or replace cartilage in a joint in the body, such as a knee joint including a knee medial compartment joint, a patellofemoral joint, and a total knee joint, a knee meniscus, a condyle, a patella, a tibial plateau, ankle joint, an elbow joint, a shoulder joint including a labral joint, a hand joint including a metacarpal joint, a finger joint, a thumb joint, and a base of thumb joint, a glenoid, a hip joint including an acetabular joint, an intervertebral disc, vertebral joint, including an intervertebral facet joint, a labrum, a meniscus, a foot joint, including a metatarsal joint and a toe joint, a jaw joint, including a temporomandibular joint, or a wrist joint and any portion thereof.

In some embodiments, the implants described herein may have at least a portion of the implant that is configured to transiently deform during implant placement in a joint.

Still another aspect of the disclosure provides a method of repairing an orthopedic joint including the steps of replacing natural cartilage with a water-swellable mixed anion IPN or semi-IPN in accordance with the present disclosure, including engaging the mixed anion IPN or semi-IPN with a bone surface defining the joint. The method may also include the steps of bonding, suturing, stapling, and/or screwing the mixed anion IPN or semi-IPN to the hone surface. The method may also include incorporating the material as a bearing component of another device, such as a metal-based prosthesis. The method may also include the step of inserting a stem portion into the bone surface. The orthopedic joint may be selected from a group consisting of a shoulder joint including a labral joint, a hip joint including an acetabular joint, a wrist joint, a finger joint, a hand joint, including a metacarpal joint, a thumb joint, a base of thumb joint, an ankle joint, elbow joint, a foot joint, including a metatarsal joint and a toe joint, a jaw joint, including a temporomandibular joint, a knee medial compartment joint, a patellofemoral joint, a total knee joint, a femoral joint, an acetabular joint, an elbow, an intervertebral facet, and a vertebral joint, including an intervertebral facet joint.

Yet another aspect of the disclosure provides a marine hull coating including a water-swellable mixed anion IPN or semi-IPN in accordance with the present disclosure, the coating having a hull contact surface adapted to attach to a marine hull. The coating may also include an ultraviolet light protection agent and/or an anti-oxidation agent.

BRIEF DESCRIPTION OF THE DRAWINGS

(FIG. 3A) 17.6% PAA/PEU, (FIG. 3B) 22.2% PAA/PEU. (FIG. 3C 25.5% PAA/PEU, (FIG. 3D) 27.6% PAA/PEU, (FIG. 3E) 40.7% PAA/PEU, (FIG. 3F) non-sulfonated gradient PEU-PAA test article with 40.7% PAA/PEU. For all test articles made with different amount of PAA/PEU percentage a line was fitted to derive the percent weight loss per millimolar of total divalent ion concentration and the slope is indicate on the top of each sub-figure. Error bars represent standard error; n=5 for each point. NS: p<0.1.

DETAILED DESCRIPTION OF THE DISCLOSURE

Figure 1:
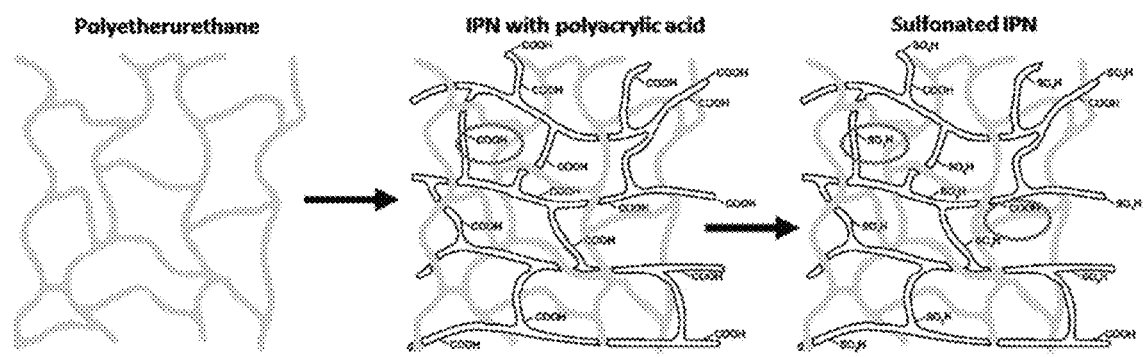
FIG. 1 is a schematic illustration of a process of forming an IPN or semi-IPN according to one aspect of this present disclosure. From left to right: the thermoplastic material in this aspect of this present disclosure is polyurethane that is converted to a semi-IPN of polyurethane and poly(acrylic acid). Then the carboxylic moieties are derivatized to sulfonic moieties.

The present disclosure includes processes for modifying common commercially available hydrophobic thermoset or thermoplastic polymers to confer upon them qualities such as lubricity, permeability, conductivity and wear-resistance. Such hydrophobic polymers ordinarily do not soak up water and are generally useful for their mechanical strength, impermeability and insulating ability. An exemplary list of hydrophobic polymers modifiable by the process of this disclosure includes the following: Acrylonitrile butadiene styrene (ABS), Polymethylmethacrylate (PMMA), Acrylic, Celluloid, Cellulose acetate. Ethylene-Vinyl Acetate (EVA), Ethylene vinyl alcohol (EVAL), Kydex, a trademarked acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone). Polyhydroxyalkanoates (PHAs), Polyketone (PK), Polyester. Polyetheretherketone (PEEK), Polyetherimide (PEI), Polyethersulfone (PES)—see Polysulfone, Polyethylenechlorinates (PEC). Polyimide (PI). Polymethylpentene (PMP), Polyphenylene oxide (PPO), Polyphenylene sulfide (PPS), Polyphthalamide (PPA), Polystyrene (PS), Polysulfone (PSU), Polyvinyl acetate (PVA), Polyvinyl chloride (PVC), Polyvinylidene chloride (PVDC), Spectralon, Styrene-acrylonitrile (SAN), Polydimethylsiloxane (PDMS), and Polyurethanes (PU). A wide variety of polyurethanes can be used with varying hard segment, soft segment, and chain extender compositions, as will be described herein.

One aspect of the disclosure takes advantage of a characteristic of some modifiable thermoset or thermoplastic hydrophobic polymers: the presence of ordered and disordered (amorphous) domains within the polymer. For example, some hydrophobic thermoset or thermoplastic polymers such as polyurethanes are phase-separated, containing first domains of hard segments and second domains of soft segments, with the two domains exhibiting different solubility properties with respect to interpenetration of monomers. In polyurethanes, the hard segments are disposed primarily within the ordered domains and the soft segments are disposed primarily within the disordered (amorphous) domains. (The starting polymer may contain more than two domains, of course, without departing from the scope of the disclosure.) This difference in properties between the two domains of the phase-separated polymer enables the process of this disclosure to impart new properties to the polymer that can extend throughout the bulk of the material or throughout only a portion of the material. e.g., in a particular region or in a gradient. For example, a non-lubricious polymer can be made lubricious; an otherwise non-conductive polymer can be made conductive; and an otherwise non-permeable polymer can be made permeable. Moreover, the process can be performed repeatedly to introduce more than one new property to the starting polymer.

In some embodiments, phase separation in the polymer allows for differential swelling of one or more separated phases within the polymer with, e.g., a solvent and/or monomer, which is then used to impart new properties. According to the disclosure, for example, lubriciousness can be introduced to an otherwise non-lubricious material by adding and polymerizing one or more carboxylic-acid-group-containing monomers, followed by reaction with one or more sulfonic-acid-containing compounds. In one embodiment, a polymer material with high mechanical strength and a lubricious surface can be made from an otherwise non-lubricious, hydrophobic polymer. By converting otherwise hydrophobic materials into multi-phasic materials with both solid and liquid (water) phases, the present disclosure addresses a need in the art for lubricious, high strength materials for use in medical, commercial, and industrial applications.

In some embodiments, a thermoplastic polyurethane-based polymer containing a network of hard segments and soft segments may be swollen with monomer and optional solvent, along with an initiator and cross-linker, such that the soft segments are swollen while mostly not affecting the hard segment material. This swelling process is not dissolution of the polymer; rather, the hard segments act as physical crosslinks to hold the material together as the soft segments are imbibed with the monomer(s) and optional solvent(s). After polymerization and cross-linking of the monomers and after reaction with a sulfonic-acid-containing compound, a second network is formed in the presence of the first network, creating an IPN or semi-IPN in which the second polymer (i.e., the polymerized and sulfonated monomer) is primarily sequestered within the soft, amorphous domain of the first polymer. Despite some degree of molecular rearrangement and further phase separation, the hard segments largely remain ordered and crystalline, providing structure and strength to the material.

The new properties provided by this IPN depend on the properties of the polymerized monomers that were introduced and on the sulfonic-acid-containing compounds that are subsequently introduced. Examples of such new properties include lubriciousness, conductivity, hardness, absorbency, permeability, photoreactivity and thermal reactivity. After optional swelling in a buffered aqueous solution, the second network of the mixed anion IPN or semi-IPN is ionized, and the mixed anion IPN or semi-IPN is water-swollen and lubricious. Thus, hydrophilicity (i.e., water absorbency) can be introduced into an otherwise hydrophobic material. A hydrophobic polymer material such as polyurethane or ABS can be infiltrated with various mixed anion polymers (polymers comprising a combination of underivatized carboxylic acid groups and amino-sulfonic-acid-derivatized carboxylic acid groups) such that it absorbs water.

In addition to absorbency, various levels of permeability (water, ion, and/or solute transport) can be introduced into an otherwise non-permeable material. For example, a hydrophobic polymer material such as polyurethane or ABS can be infiltrated with a mixed anion polymer so that it absorbs water, as described above. This hydration of the bulk of the material allows for the transport of solutes and ions. The transport of solutes and ions and permeability to water is made possible by phase continuity of the hydrated phase of the mixed anion IPN or semi-IPN. This may be useful in various applications, including drug delivery, separation processes, proton exchange membranes, and catalytic processes. The permeability can also be utilized to capture, filter, or chelate solutes as a liquid flows over or through the material. Furthermore, because of this permeability, the materials of the present disclosure can be bestowed with increased resistance to creep and fatigue relative to their component hydrophobic polymers due to their ability to re-absorb fluid after sustained or repetitive loading.

Also, any of the domains can be doped with any number of materials, such as antioxidants, ions, ionomers, contrast agents, particles, metals, pigments, dyes, biomolecules, polymers, proteins and/or therapeutic agents. Any of these materials can be incorporated physically or chemically (e.g., covalently bonded into or otherwise included as one or more of the constituents of the IPN or semi-IPN).

The hydrophobic thermoset or thermoplastic polymer can be additionally crosslinked or copolymerized with the carboxylic-acid-group-containing polymer if, for example, acryloxy, methacryloxy, acrylamido, allyl ether, or vinyl functional groups are incorporated into one end or both ends of the thermoset or thermoplastic polymer and then cured by UV or temperature in the presence of an initiator. For instance, a polyurethane dimethacrylate or polyurethane bisacrylamide can be used in the first network by curing in the presence of a solvent (such as dimethylacetamide) and then evaporating the solvent. The addition of chemical crosslinks (rather than just physical crosslinks) to the IPN adds a level of mechanical stability against creep or fatigue caused by continuous, dynamic loading.

In addition, in the case where the thermoplastic polymer is a polyurethane, a multi-arm (multifunctional) polyol or isocyanate can be used to create crosslinks in the polyurethane. In this case, a fully interpenetrating polymer network is created (rather than a semi-interpenetrating polymer network). The result is a composite material with the high strength and toughness of polyurethane and the lubricious surface and multi-phasic bulk behavior of the ionic polymer. Alternatively, other crosslinking methods can be used, including but not limited to gamma or electron-beam irradiation. These features useful for bearing applications such as artificial joint surfaces, or as more biocompatible, thrombo-resistant, long-term implants in other areas of the body such as the vascular system or the skin. Being swollen with water also allows imbibement with solutes such as therapeutic agents or drugs for localized delivery to target areas of the body.

In another embodiment of the present disclosure, the hydrophobic thermoset or thermoplastic polymer can be linked to the carboxylic-acid-group-containing polymer. For example, polyurethane can be linked through a vinyl-end group. Depending on the reactivity ratio between the end group and the monomer being polymerized, different chain configurations can be yielded. For instance, if the reactivity of the monomer with itself is much greater than the end group with the monomer, then the carboxylic-acid-group-containing polymer will be almost completely formed before the addition to the chain. On the other hand, if the reactivity of the monomer and the end group are similar, then a random grafting-type copolymerization will occur. The monomers and end groups can be chosen based on their reactivity ratios by using a table of relative reactivity ratios published in, for example, The Polymer Handbook. The result of these will be a hybrid copolymer/interpenetrating polymer network.

Any number or combinations of ethylenically unsaturated monomers or macromonomers (i.e., with reactive double bonds/vinyl groups) can be used alone or in combination with various solvents and selectively introduced into one or more of the phases of the polymer as long as at least a portion of such monomers contain carboxylic acid functional groups. Other monomers include but are not limited to dimethylacrylamide, acrylamide, N-isopropylacrylamide (NIPAAm), methyl acrylate, methyl methacrylate, hydroxyethyl acrylate/methacrylate.

In one embodiment, a preformed, thermoplastic polymer may be immersed in acrylic acid (or in a solution of acrylic acid (1%-1%40 or other vinyl monomer solution) along with crosslinker (e.g., triethylene glycol dimethacrylate or N,N'-methylene bisacrylamide) and photoinitiator (e.g. 2-hydroxy-2-methyl propiophenone). The acrylic acid solution can be based on water, salt buffer, or organic solvents such as dimethylacetamide, acetone, ethanol, methanol, isopropyl alcohol, toluene, dichloromethane, propanol, dimethylsulfoxide, dimethyl formamide, or tetrahydrofuran. The polymer may be swollen by the monomer (e.g., due to solvation of the soft segments in the polymer). The monomer content in the swollen polymer can range from as little as about 1% to up to about 90%.

It is noted that although various aspects of the disclosure are illustrated herein using acrylic acid as an exemplary monomer, it should be understood that various monomers having carboxylic acid groups are also contemplated, including one or more of the following, among others: acrylic acid, methacrylic acid, crotonic acid, linolenic acid, maleic acid, and fumaric acid. Similarly, it is noted that although various aspects of the disclosure are commonly illustrated herein using poly(acrylic acid) as an exemplary polymer, it should be understood that polymers of various monomers having carboxylic acid groups may also be applicable, including one or more of the following, among others: acrylic acid, methacrylic acid, crotonic acid, linolenic acid, maleic acid, and fumaric acid.

The monomer-swollen polymer may then be removed, placed in a mold made of glass, quartz, or a transparent polymer, then exposed to UV light (or elevated temperature) to initiate polymerization and crosslinking of the monomers. Alternatively, instead of using a mold, the monomer-swollen polymer can be polymerized while fully or partially exposed to air or an inert atmosphere (e.g., nitrogen or argon), or alternatively in the presence of another liquid such as an oil (e.g., paraffin, mineral, or silicone oil). Depending on the initiator used, exposure to UV light, IR, or visible light, a chemical, electrical charge, or elevated temperature leads to polymerization and crosslinking of the carboxylic-acid-group-containing monomers within the hydrophobic polymer. As an example, monomers (e.g. acrylic acid) are polymerized to form an ionic polymer comprising carboxylic acid groups within a preformed thermoplastic, hydrophobic matrix, forming an interpenetrating polymer network ("IPN"). Solvents can be extracted out by heat and convection or by solvent extraction. Solvent extraction involves the use of a different solvent (such as water) to extract the solvent from polymer, while heat or convection relies upon evaporation of the solvent.

Sulfonation of the IPN may then be conducted through an amidation reaction of carboxylic acid groups with an amino sulfonic acid compound such as taurine using 4-(4,6-Dimethoxy-1,3,5-triazin-2-yl)-4-methylmorpholinium chloride as the catalyst.

Swelling of the mixed anion IPN or semi-IPN in aqueous solution such as phosphate buffered saline (or other salt solution such as the divalent cation solutions described elsewhere herein) at neutral pH will lead to ionization of the caboxylic acid and sulfonic acid groups and further swelling with water and salts. The resulting swollen mixed anion IPN or semi-IPN will have a lubricious surface conferred by the hydrophilic, charged polymer and high toughness and mechanical strength conferred by the thermoplastic. In the case of a polyurethane-based mixed anion IPN or semi-IPN, the mixed anion IPN or semi-IPN will have a structure in which crystalline hard segments in the polyurethane act as physical crosslinks in the first network, while chemical crosslinks will be present in the second network.

The materials can also be crosslinked after synthesis using gamma radiation or electron beam radiation. In one example, polyurethane/polyacrylic acid can be synthesized and then crosslinked by gamma irradiation, for instance with doses of, for example, 5, 10, 15, 20, or 25 kGy. In this case the polymerization of polyacrylic acid would be done in the absence of a crosslinker, and after formation of the polymer blend (physical IPN), the material would be exposed to gamma radiation. It is known in the art that crosslinking of poly(acrylic acid) hydrogels using gamma irradiation shows a dose-dependence to the crosslinking of the polymer. In the case of the polyurethanes, the polyurethane polymer can be a commercially available material, a modification of a commercially available material, or be a new material.

Any number of chemistries and stoichiometries can be used to create the polyurethane polymer. For the hard segment, isocyanates used are 1,5 naphthalene diisocyanate (NDI), isophorone isocyanate (IPDI), 3,3-bitoluene diisocyanate (TODI), methylene bis (p-cyclohexyl isocyanate) ($H_{12}$MDI), cyclohexyl diisocyanate (CHDI), 2,6 tolylene diisocyanate or 2,4 toluene diisocyanate (TDI), hexamethyl diisocyanate, or methylene bis(p-phenyl isocyanate). For the soft segment, chemicals used include, for example polyalkylene oxides, such as polyethylene oxide (PEO), polypropylene oxide (PPO), polybutylene oxide (PBO), polybutadiene, polydimethylsiloxane (PDMS), polyethylene adipate, polycaprolactone, polytetramethylene adipate, polyisobutylene, polyhexamethylene carbonate glycol, poly (1,6 hexyl 1,2-ethyl carbonate. Any number of telechelic polymers can be used in the soft segment, if end-groups that are reactive with isocyanates are used. For instance, hydroxyl- or amine-terminated poly(vinyl pyrolidone), dimethylacrylamide, carboxylate or sulfonated polymers, telechelic hydrocarbon chains (with hydroxyl and/or amine end groups), dimethylolpropionic acid (DMPA), or these in combination with each other or with other soft segments mentioned above (e.g., PDMS) can be used.

Chain extenders include, for example, 1,4-butanediol, ethylene diamine. 4,4'-methylene bis (2-chloroaniline) (MOCA), ethylene glycol, and hexane diol. Any other compatible chain extenders can be used alone or in combination. Crosslinking chain extenders can be used containing isocyanate-reactive end groups (e.g. hydroxyl or amine) and a vinyl-based functional group (e.g. vinyl, methacrylate, acrylate, allyl ether, or acrylamide) may be used in place of some or all of the chain extender. Examples include 1,4-dihydroxybutene and glycerol methacrylate. Alternatively, crosslinking can be achieved through the use of a polyol such as glycerol which contains greater than two hydroxyl groups for reaction with isocyanates.

In some embodiments, at least 1% of the monomers in the second network comprise carboxylic acid groups. In one such embodiment, poly(acrylic acid) (PAA) hydrogel is used as the second polymer network, formed from an aqueous solution of acrylic acid monomers. Other carboxylic-acid-group-containing monomers include, for example, methacrylic acid. These other monomers can also be in a range of 1%-99% in either water or organic solvent, or may be in pure (100%) form. One embodiment of the monomer used to form the second network can be described by the following characteristics: (1) it is capable of swelling without dissolving the polyurethane, (2) capable of polymerizing, and (3) is carboxylic-acid-group-containing.

Other embodiments use an additional co-monomer which may be non-ionic, such as acrylamide, methacrylamide. N-hydroxyethyl acrylamide, N-isopropylacrylamide, methylmethacrylate, N,N-Dimethylacrylamide, N-vinyl pyrrolidone, 2-hydroxyethyl methacrylate, 2-hydroxyethyl acrylate or derivatives thereof.

Any type of compatible cross-linkers may be used to crosslink the second network in the presence of any of the aforementioned first networks such as, for example, ethylene glycol dimethacrylate, ethylene glycol diacrylate, diethylene glycol dimethacrylate (or diacrylate), triethylene glycol dimethacrylate (or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene) bisacrylamide, derivatives, or combinations thereof. Any number of photoinitiators can also be used depending on their solubility with the precursor solutions/materials. These include, but are not limited to, 2-hydroxy-2-methyl-propiophenone and 2-hydroxy-1-[4-(2-hydroxyethoxy) phenyl]-2-methyl-1-propanone. In addition, other initiators such as benzoyl peroxide, 2-oxoglutaric acid, azobisisobutyronitrile, or potassium persulfate (or sodium persulfate) can be used. For instance, benzoyl peroxide is useful for temperature-initiated polymerizations, while azobisisobutyronitrile and sodium persulfate are useful as radical initiators.

In another embodiment, a solvent can be used as a vehicle to deliver monomers that otherwise would not mix (or solubilize with) the polymer to one (or more) phases of the polymer. The solvent must be carefully chosen based on the specific qualities and phases of the polymer and monomers. For instance, acetic acid is capable of swelling but does not dissolve many polyurethanes. Therefore, acetic acid can be used to carry other monomers such as an acrylamide solution, that otherwise would not enter polyurethane, into the bulk of the polyurethane. This allows the acrylamide to be selectively polymerized inside one phase of the polyurethane. The acetic acid can then be washed out leaving behind a polyurethane with one or more new properties. Other solvents that can be used include, but are not limited to, methanol, propanol, butanol, (or any alkyl alcohol), acetone, dimethylacetamide, tetrahydrofuran, diethyl ether, or combinations of these. Taking into account the solubilities in the phases of the polymer, solvents with varying degrees of swelling of one can be chosen. Solubilities of the solvents and components of the material to be swollen can be obtained from polymer textbooks such as The Polymer Handbook or can be measured experimentally.

Figure 2:
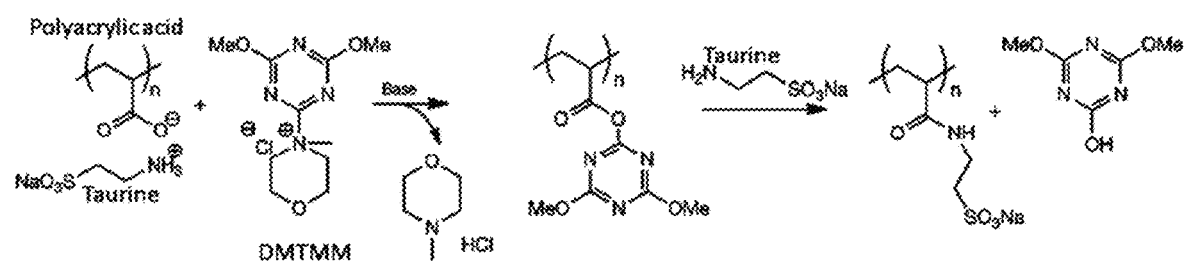
FIG. 2 is a schematic illustration of a sulfonation process according to one aspect of this present disclosure. The poly(acrylic acid) of the semi-IPN is reacted with taurine and (4-(4,6-dimethoxy-1,3,5-triazin-2-yl)-4-methyl-morpholinium chloride) in basic conditions to derive the poly (sulfonic acid) derivative of poly(acrylic acid) and taurine.
Figure 3A:
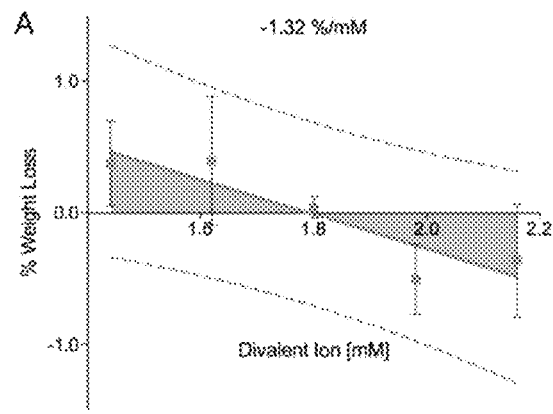
FIGS. 3A-3E illustrate divalent percent weight loss of sulfonated (FIG. 3A-E) and non-sulfonated (FIG. 3F) gradient poly(ether urethane)-poly(acrylic acid) (PEU-PAA) test articles across a range of PAA/PEU percentages as a function of the total divalent ion concentration.
Figure 3B:
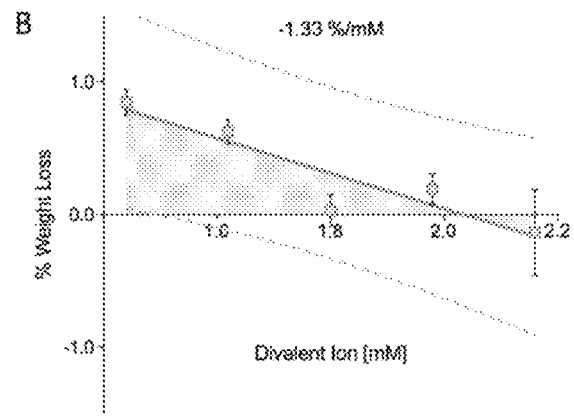
Figure 3C:
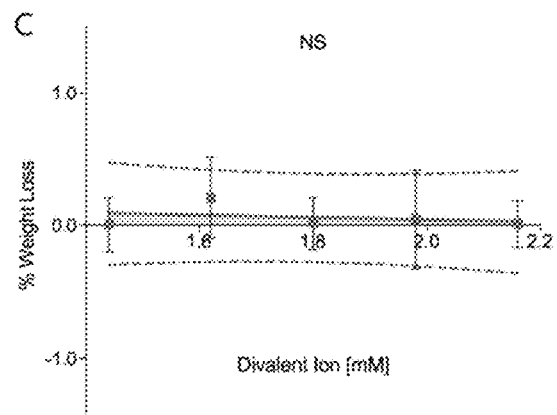
Figure 3D:
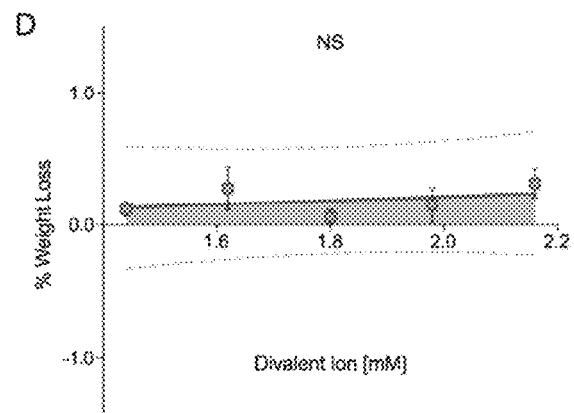
Figure 3E:
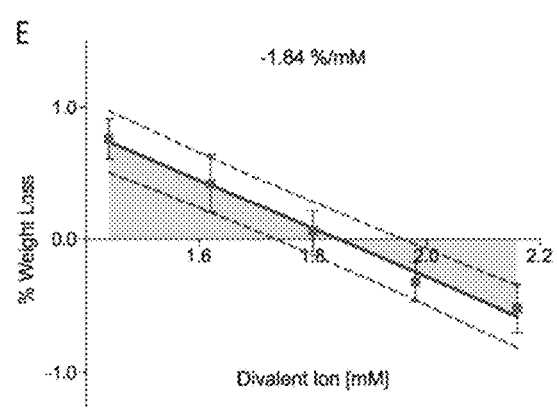
Figure 3F:
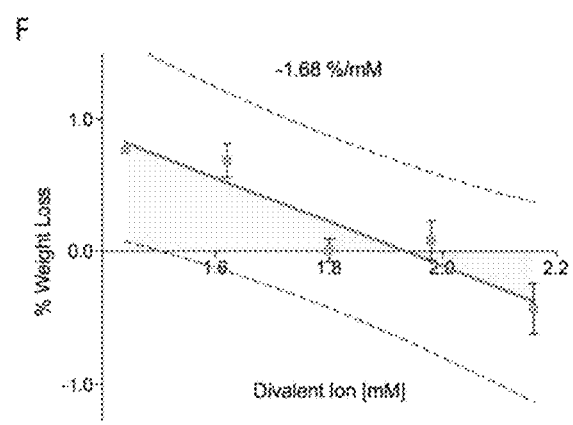

After polymerization of the carboxylic-acid-group containing monomers, any optional co-monomers and any cross-linkers, the resulting composition is then reacted with one or more sulfonic-acid-containing compounds to sulfonate a portion of the carboxylic-acid-group containing monomers to complete the second network. In certain embodiments, the sulfonation of a precursor IPN or semi-IPN having carboxylic acid groups is accomplished through an amidation reaction with taurine using 4-(4,6-Dimethoxy-1,3,5-triazin-2-yl)-4-methylmorpholinium chloride as the catalyst. The chemical reaction process to create the mixed anion IPN or semi-IPN is depicted in FIG. 1. The sulfonation chemistry used to convert the carboxylic acid groups to sulfonate groups is shown in FIG. 2. Of course, the process is not limited to PAA but is also applicable to virtually any polymer containing carboxylic acid groups.

Among the applications of the disclosure are the creation of hydrophilic, lubricious sidings or coatings to reduce biofilm formation and/or barnacle formation in marine vessels, other water crafts or water-borne objects, or pipes. In addition, the disclosure can be used as a method for making bearings and moving parts for applications such as engines, pistons, or other machines or machine parts. The disclosure can also be used in artificial joints systems or long-term implants in other areas of the body, such stents and catheters for the vascular or urinary system or implants, patches, or dressings for the skin.

The present disclosure can be used to create a composition gradient within a starting homogenous polymeric material. A gradient can be formed in material along a thickness direction, with the mixed anion IPN or semi-IPN formed on one side and extending in a diminishing concentration to another side. e.g., substantially only the starting polymeric material. The mixed anion IPN or semi-IPN concentration gradient may be radial within material, with the outer surface being the highest concentration of mixed anion IPN or semi-IPN and the center or core having the lowest concentration of mixed anion IPN or semi-IPN. In one method of fabricating a thermoplastic gradient mixed anion IPN or semi-IPN according to the present disclosure, one side of the thermoplastic material is imbibed with a monomer solution along with a photoinitiator and a crosslinker, and then the monomer is polymerized and crosslinked (e.g., with UV light) within the thermoplastic to form a gradient mixed anion IPN or semi-IPN. In one embodiment, a mixed anion IPN or semi-IPN can be created in a gradient hydrophobic polymer is swollen in carboxylic-acid-containing monomer on one side only or if the swelling time is limited such that diffusion of the monomers through the bulk of the hydrophobic polymer is not complete. This is especially useful in the creation of osteochondral grafts for orthopedic joint replacement materials. For instance, in the case of a cartilage replacement material, one side of the material is made lubricious and water swollen, while the other remains a solid (pure thermoplastic). Alternatively, bulk materials with a mixed anion IPN or semi-IPN outer aspect and hydrophobic-polymer-only "core" can be made if the diffusion of carboxylic-acid-containing monomer into the hydrophobic polymer is precisely controlled by timing the infiltration of the monomers into the bulk. The differential swelling that results from this configuration can lead to remaining stresses (compressive on the swollen side, tensile on the non-swollen side) that can help enhance the mechanical and fatigue behavior of the material. In the case of a material with a thickness gradient, the base of hydrophobic-polymer-only material can be used for anchoring, adhering, or suturing the device to the anatomical region or interest. This base can be confined to a small area or be large (e.g., a skirt) and can extend outward as a single component or multiple components (e.g., straps). The internal stresses built up within the thermoplastic during processing or after swelling can be reduced by temperature-induced annealing. For instance, temperatures of 60-120 degrees Celsius may be used for various times (30 minutes to many hours) to anneal the polymer, and the heat can be applied in an oven, by a hot surface, by radiation, or by a heat gun. The thermoplastic can later be crosslinked using, for example, gamma or electron beam radiation.

Articles made from the mixed anion IPN's and semi-IPN's of this disclosure may also be formed in a laminate structure. In one example, the mixed anion IPN or semi-IPN structure is comprised of a hydrophilic polymer such as sulfonated poly(acrylic acid) (sPAA) that is interpenetrating a first thermoplastic such as polyether urethane, which is formed on top of a second thermoplastic such as polycarbonate urethane. The first and second thermoplastics can be themselves comprised of multiple layers of various hardnesses and properties. In addition, many more than two thermoplastic layers can be used, and one or more of the thermoplastics can be crosslinked. Finally, non-thermoplastic elements can be incorporated into this construct.

Heat can be used to re-anneal the physical crosslinks in the polymer (e.g., the hard segments in the polyurethane) in the hydrophobic-polymer side of the gradient mixed anion IPN or semi-IPN to lead to different desired curvatures after bending (e.g., over a mold or template) and cooling, including both convex and concave curvatures on the hydrophobic-polymer side of the gradient mixed anion IPN or semi-IPN. Other shapes may be formed, of course, as desired. The use of thermoplastic as a hydrophobic polymer facilitates molding of a device to a desired shape by, for example, injection molding, reactive injection molding, compression molding, or alternatively, dip-casting. The molded device can then be subjected to subsequent network infiltration and polymerization steps to yield the new mixed anion IPN or semi-IPN material.

Shaping of mixed anion IPN and semi-IPN articles according to this disclosure may be performed in situ, such as within a human body, for example, by heating of a thermoplastic mixed anion IPN or semi-IPN to enable it to wrap around the curvature of a femoral head or to enable it to adapt to the curvature of a hip socket.

Shaped or unshaped mixed anion IPN and semi-IPN articles made according to this disclosure may be attached to other surfaces. For example, a bonding agent such as a solvent, cement, or glue can be used to attach the thermoplastic gradient mixed anion IPN or semi-IPN article to a surface at a bonded interface. Addition of the solvent, for example, causes the material to dissolve locally, and after contact with a surface and drying of the solvent, the thermoplastic adheres to the surface. This approach can be used to attach a gradient mixed anion IPN or semi-IPN to bone surfaces in joints. The bonding agent may be sterile in a disposable syringe in certain embodiments.

In specific embodiments, the bonding agent may comprise a urethane dimethacrylate and methyl methacrylate (MMA). The bonding agent may be cured using radiation, such as visible light, infrared light, or ultraviolet light using a photoinitiator; it may be cured using a thermal initiator, chemical initiator or catalysts, and/or redox activated initiation systems, for example, one comprising camphorquinone and N,N-Dimethyl-p-toluidine. A combination of photo-initiation and non-light-based initiation systems such as thermal, chemical, and/or redox systems may be used. An accelerating agent may also be used. The urethane dimethacrylate may comprise soft segments selected, for example, from polyalkylene oxides, such as polyethylene oxide (PEO), polypropylene oxide (PPO), and polybutylene oxide (PBO), polybutadiene, polydimethylsiloxane (PDMS), polyethylene adipate, polycaprolactone, polytetramethylene adipate, polyisobutylene, polyhexamethylene carbonate glycol, and poly (1,6 hexyl 1,2-ethyl carbonate). The urethane dimethacrylate may comprise hard segments formed, for example, from 1,5 naphthalene diisocyanate (NDI), isophorone isocyanate (IPDI), 3,3-bitoluene diisocyanate (TODI), methylene bis (p-cyclohexyl isocyanate) (H MDI)), cyclohexyl diisocyanate, 2,6 tolylene diisocyanate or 2,4 toluene diisocyanate (TDI), hexamethyl diisocyanate, or methylene bis(p-phenyl isocyanate). The urethane dimethacrylate component may comprise, for example, about 70-90% by weight of the bonding agent.

In general, in one embodiment, a system is provided including an article comprising a mixed anion IPN or semi-IPN of the present disclosure and an adhesive kit comprising a bonding agent (e.g., such as a solvent, cement, or glue).

In general, in one embodiment, a packaged article is provided that comprises an article comprising a mixed anion IPN or semi-IPN in accordance with the present disclosure. In some embodiments, a divalent-cation-containing solution comprising one or more divalent metal cations is contained within the sterile package.

This and other embodiments can include one or more of the following features. The adhesive kit can include a first reservoir including a first mixture including at least one of a urethane dimethacrylate oligomer and a methyl methacrylate monomer; at least one of a photoinitiator and a thermal initiator; and an inhibitor: a second reservoir including a second mixture including at least one of a urethane dimethacrylate monomer and a methyl methacrylate monomer; and an accelerator; and an instruction for use; wherein at least one of the first reservoir and the second reservoir can include a urethane dimethacrylate monomer and at least one of the first reservoir and the second reservoir can include a methyl methacrylate monomer.

Both the first reservoir and the second reservoir can include a urethane dimethacrylate monomer and a methyl methacrylate monomer. The second reservoir can further include an inhibitor. The system can further include poly (methyl methacrylate). The system can further include a third reservoir including a poly(methyl methacrylate) powder. The first mixture, the second mixture and the poly (methyl methacrylate) can define a component weight, and a weight of the poly(methyl methacrylate) powder can include from about 1% to about 70% of the component weight. The system can further include a polystyrene. The system can further include a photoinitiator and a thermal initiator. The first reservoir can include a first chamber in a syringe and the second reservoir can include a second chamber in the syringe, wherein the syringe can be configured to combine the first mixture with the second mixture to create an adhesive mixture. The system can further include a nozzle connected with the syringe configured to dispense the adhesive mixture. The first reservoir and the second reservoir each can include from about 0% (w/w) to about 100% (w/w), typically, from about 1% (w/w) to about 99% (w/w), urethane dimethacrylate oligomer and/or 0% (w/w) to about 100% (w/w), typically, from about 1% (w/w) to about 99% (w/w), methyl methacrylate. The first reservoir and/or the second reservoir each can include from about 0% (w/w) to about 100% (w/w), typically, from about 1% (w/w) to about 99% (w/w), methyl methacrylate. The at least one initiator can include a photoinitiator including between 0% (w/w) and about 5% (w/w), typically, from about 1% (w/w) to about 5% (w/w), camphorquinone. The at least one initiator can include a thermal initiator including between 0% (w/w) and about 5% (w/w), typically, from about 1% (w/w) to about 5% (w/w), benzoyl peroxide. The accelerator can include between 0% (w/w) and about 5% (w/w), typically, from about 1% (w/w) to about 5% (w/w), N,N-dimethyl-p-toluidine. The inhibitor can include between 0% (w/w) and about 5% (w/w), typically, from about 1% (w/w) to about 5% (w/w), hydroquinone. The system can further include an additive configured to prevent an infection. The system can further include an antibiotic. The system can further include a radiopaque material. The first mixture can define a viscosity between about 1 Pa·s and 5000 Pa·s.

In one embodiment, the adhesive kit can be comprised by a single reservoir that contains from about 0% (w/w) to about 100% (w/w), typically, from about 1% (w/w) to about 99% (w/w), urethane dimethacrylate oligomer and/or 0% (w/w) to about 100% (w/w), typically, from about 1% (w/w) to about 99% (w/w), methyl methacrylate, from about 0% (w/w) to about 100% (w/w), typically, from about 1% (w/w) to about 99% (w/w), methyl methacrylate, an optional initiator (which can include, for example, at least one of a photoinitiator and a thermal initiator), typically in an amount from about 0% (w/w) to about 5% (w/w), for example, from about 1% (w/w) to about 5% (w/w), and an optional accelerator, typically in an amount from about 0% (w/w) to about 5% (w/w), for example, from about 1% (w/w) to about 5% (w/w). The single reservoir can include a chamber in a syringe. The system can further include a nozzle connected with the syringe configured to dispense the curable adhesive. The initiator can include a photoinitiator including between 0% (w/w) and about 5% (w/w), typically, from about 1% (w/w) to about 5% (w/v), camphorquinone. The accelerator can include between 0% (w/w) and about 5% (w/w), typically, from about 1% (w/w) to about 5% (w/w), N,N-dimethyl-p-toluidine. The inhibitor can include between 0% (w/w) and about 5% (w/w), typically, from about 1% (w/w) to about 5% (w/w), hydroquinone. The system can further include an additive configured to prevent an infection. The system can further include an antibiotic. The system can further include a radiopaque material. The first mixture can define a viscosity between about 1 Pa·s and 5000 Pa·s.

The mixed anion IPN and semi-IPN compositions of this disclosure, formed. e.g., by the methods of this disclosure, may be used in a variety of settings. One particular use is as artificial cartilage in an osteochondral graft. The present disclosure provides a bone-sparing arthroplasty device based on an interpenetrating polymer network that mimics the molecular structure, and in turn, the elastic modulus, fracture strength, and lubricious surface of natural cartilage. Emulating at least some of these structural and functional aspects of natural cartilage, the mixed anion semi-PNs and anion IPNs of the present disclosure form the basis of a novel, bone-sparing, "biomimetic resurfacing" arthroplasty procedure. Designed to replace only cartilage, such a device is fabricated as a set of flexible, implantable devices featuring lubricious articular surfaces and osteointegrable bone-interfaces.

In principle, the device can be made for any joint surface in the body. For example, a device to cover the tibial plateau will require an analogous bone-preparation and polymer-sizing process. For a device to cover the femoral head in the hip joint, a cap shaped device fits snugly over the contours of the femoral head. For a device to line the acetabulum, a hemispherical cup-shaped device stretches over the lip and can be snapped into place in the socket to provide a mating surface with the femoral head. In this way, both sides of a patient's hip joint can be repaired, creating a cap-on-cap articulation. However, if only one of the surfaces is damaged, then only one side may be capped, creating a cap-on-cartilage articulation. In addition, the materials of the present disclosure can be used to cap or line the articulating surfaces of another joint replacement or resurfacing device (typically comprised of metal) to serve as an alternative bearing surface.

To create a cap-shaped device using the present disclosure for the shoulder joint (also a ball-and-socket joint), a process similar to that of the hip joint is used. For instance, a shallow cup can be created to line the inner aspect of the glenoid. Furthermore, devices for other joints in the hand, fingers, elbow, ankles, feet, and intervertebral facets can also be created using this "capping" concept. In one embodiment in the distal femur, the distal femur device volume follows the contours of the bone while sparing the anterior and posterior cruciate ligaments.

The mixed anion IPN and semi-IPN of the present disclosure may be used as a cartilage replacement plug in joints of the body where cartilage has been damaged, as described below.

The mixed anion IPN and semi-IPN of this disclosure, made, for example, according to the methods of this disclosure, may be used as a fully or partially synthetic osteochondral graft. The osteochondral graft consists of a lubricious, cartilage-like synthetic bearing layer that may be anchored to porous bone or a synthetic, porous bone-like structure. The bearing layer has two regions: a lubricious surface layer and a stiff, bone anchoring layer. In one embodiment, the top, lubricious region of the bearing layer consists of an interpenetrating polymer network that is composed of two polymers. The first polymer may be a hydrophobic thermoplastic with high mechanical strength, including but not limited to polyether urethane, polycarbonate urethane, silicone polyether urethane, and silicone polycarbonate urethanes, or these materials with incorporated urea linkages, or these materials with incorporated urea linkages (e.g. polyurethane urea). The second polymer may be a hydrophilic polymer derived from carboxylic-acid-group-containing monomers, including but not limited to acrylic acid, which are subsequently subjected to a sulfonation process in which the carboxylic-acid-group-containing monomers are reacted with a sulfonic-acid-containing compound. The bottom region of the bearing layer (bone anchoring layer) may be a stiff, non-resorbable thermoplastic that can be caused to flow with ultrasonic welding vibration, ultrasonic energy, laser energy, heat. RF energy and electrical energy. The bone anchoring layer is used to anchor the bearing layer to bone or a bone-like porous structure. If porous bone is used, it can be cancellous bone from a human or animal. If a synthetic bone-like material is used, it can consist of porous calcium-phosphate (and/or other materials, including but not limited to porous carbonated apatite, beta-tricalcium phosphate, or hydroxyapatite), or a porous resorbable or non-resorbable thermoplastic as described above, including but not limited to polycarbonate urethane, polyether urethane, PLA, PLLA, PLAGA, and/or PEEK. The bearing layer is anchored to the porous bone or bone-like structure via application of pressure combined with energy that cause the bone anchoring material to melt and flow into the pores or spaces of the bone or bone-like structure, after which the energy source is removed and the material re-solidifies. The energy source can include but is not limited to vibration, ultrasonic energy, laser energy, heat, RF energy, and electrical energy.

In various embodiments, the compositions of the present disclosure can be used to form a device to partially or completely resurface damaged joints in the body of mammals (animals or human). These devices can be fixated to bone through any number of means, such as a press-fit, screws (metal or plastic, either resorbable or nonresorbable), sutures (resorbable or nonresorbable), glue, adhesives, light-curable adhesives (e.g. polyurethane or resin-based), or bonding agent (such as polymethylmethacrylate or calcium phosphate, or dental cements).

An osteochondral graft implant formed from a mixed anion IPN or semi-IPN of this disclosure can be used to replace or augment cartilage within a joint, such as a hip or shoulder joint. The implant may be slipped over the head of the humerus or femur. In some embodiments, the implant may include an opening to accommodate a ligament or other anatomical structure.

Implants and other articles may be made in a variety of complex shapes according to the disclosure. For example, osteochondral grafts may formed from a mixed anion IPN or semi-IPN of this disclosure that may be used singly or in any combination needed to replace or augment cartilage within a knee joint. For example, an osteochondral graft may be adapted to engage the femoral condyles (or alternatively, just one condyle), may be adapted to engage one or both sides of the tibial plateau, may be adapted to engage the patella and to articulate with an osteochondral graft adapted to engage the patellofemoral groove and/or may be adapted to engage the lateral and medial menisci.

Osteochondral grafts may also be used in other joints, such as in the finger, hand, ankle, elbow, feet or vertebra. Labrum prosthesis may be formed from a mixed anion IPN or semi-IPN of this disclosure for use in replacing or resurfacing the labrum of the shoulder or hip. A mixed anion IPN or semi-IPN of this disclosure may be used as a bursa osteochondral graft, labrum osteochondral graft, glenoid osteochondral graft and humeral head osteochondral graft. In some embodiments, a mixed anion IPN or semi-IPN of this disclosure may be used as prostheses for resurfacing intervertebral facets.

The mixed anion IPN's and semi-IPN's compositions of this disclosure may be formed as prosthetic cartilage plugs for partial resurfacing of joint surfaces. For example, a prosthetic cartilage plug may be formed from a gradient mixed anion IPN composition of this disclosure. Plug may have a stem portion formed on a thermoplastic side of the article and adapted to be inserted into a hole or opening in a bone. The head of the plug is formed to be a lubricious mixed anion IPN or semi-IPN, as described above. Stem may be press fit into a hole or opening in the bone, leaving the lubricious mixed anion IPN surface to be exposed to act as prosthetic cartilage.

A prosthetic cartilage plug formed from the mixed anion IPN or semi-IPN of the present disclosure, in which the stem is provided with helical ridges to form a screw for fixation of the plug to bone.

Embodiments of the composition of this disclosure may be used to make two-side lubricious implants. Implants may be sized and configured to replace an intervertebral disc. Implants may have lubricious mixed anion IPN or semi-IPN surfaces (formed, e.g., as described above) on its upper and lower sides. A knee spacer having a wedge-shaped cross-section may be formed. As with disc prosthesis, spacer also has lubricious mixed anion IPN or semi-IPN surfaces on its upper and lower sides.

Other variations and modifications to the above compositions, articles and methods are described below.

The hydrophobic polymer can be one that is available commercially or custom-made and made by many ways (e.g., extruded, injection molded, compression molded, reaction injection molded (RIM) or solution-casted.) The first polymer can be uncrosslinked or crosslinked by various means. Either polymer can be crosslinked by, e.g., gamma radiation or electron beam radiation.

Any number or combinations of ethylenically unsaturated monomers or macromonomers (e.g., containing reactive double bonds) can be used as the basis of the second or subsequent network so long as carboxylic-acid-group-containing monomers are included. These include but are not limited those containing vinyl, acrylate, methacrylate, allyl ether, or acrylamide groups. And number of pendant functional groups can be conjugated to these ethylenically unsaturated groups including but not limited to carboxylic acids, esters, alcohols, ethers, phenols, aromatic groups, or carbon chains.

The hydrophobic polymer may be a polyurethane-based polymer such as the following: polyether urethane, polycarbonate urethane, polyurethane urea, silicone polyether urethane, or silicone polycarbonate urethane. Other polyurethanes with other hard segments, soft segments, and chain extenders are possible.

Other polymers can be used as the hydrophobic polymer, such as homopolymers or copolymers of silicone (polydimethylsiloxane) or polyethylene.

When a polyurethane-based polymer is used as the hydrophobic polymer, the extent of physical and chemical crosslinking of the polyurethane-based polymer can be varied between physical crosslinking-only (thermoplastic) to extensive chemical crosslinking. In the case of chemical crosslinking, the crosslinkable polyurethane can be used alone or as a mixture with thermoplastic (uncrosslinked) polyurethane.

The conditions of polymerization (i.e., ambient oxygen, UV intensity, UV wavelength, exposure time, temperature) and sulfonation may be varied.

The orientation and steepness of the composition gradients can be varied by various means such as time and/or method of immersion in the monomer and/or amino sulfonic acid compound, and the application of external hydrostatic positive or negative pressure.

The hydrophobic polymer can be made porous by various techniques such as foaming or salt-leaching. After swelling of the porous polymer (such as PU) with a monomer (such as AA) followed by polymerization or AA and reaction with an amino sulfonic acid, a porous mixed anion IPN is formed.

Additional layers of thermoplastics can be added to material on either the IPN side or the thermoplastic side-only by curing or drying the new thermoplastic to the surface. The layers can all be the same material or be different materials (e.g. ABS+polyurethane, polyether urethane+polycarbonate urethane, etc.

A number of different solvents can be used during the synthesis of the polyurethane, the second network, or both, including but not limited to dimethylacetamide, tetrahydrofuran, dimethylformamide, ethanol, methanol, acetone, water, dichloromethane, propanol, methanol, or combinations thereof.

Any number of coupling reagents may be employed to promote the reaction of the amino sulfonic acid compounds with the carboxylic-acid-group-containing polymers, including triazine-based coupling reagents, carbodiimides, phosphonium and aminium salts and fluoroformamidinium coupling reagents. In a particular embodiment, the coupling reagent may be 4-(4,6-dimethoxy-1,3,5-triazin-2-yl)-4-methylmorpholinium chloride (DMTMM).

The degree and depth of derivatization (i.e., sulfonation) of solid articles comprising a precursor polymer having carboxylic acid groups, including PAA-based IPNs, depends on balancing the diffusion rate of the reactants with the reaction kinetics and hydrolysis rate of the coupling reagent and of the intermediate ester. One class of coupling reagents that has been used extensively for the activation and derivatization of carboxylic acids in aqueous solutions are carbodiimides. In various embodiments, an amino sulfonic acid compound such as taurine is initially diffused into a PAA-based IPN, followed by the addition of an N-substituted carbodiimide. N-substituted carbodiimides react with carboxylic acids to form highly reactive, o-acylisourea intermediates that are pH dependent and tend to hydrolyze within seconds at near physiological pH (Hoare, D G. and Koshland, D E J. (1967) 'A method for the quantitative modification and estimation of carboxylic acid groups in proteins'. *Journal of Biological Chemistry,* 242(10), pp. 2447-2453). After hydrolysis, the intermediate ester is converted back to the carboxylic acid and an inactive N-acylurea. This immediate hydrolysis in effect consumes the coupling reagent before it diffuses within the bulk of the IPN and react with the primary amine of the amino sulfonic acid compound. Lowering the pH can reduce the hydrolysis rate of the intermediate ester, but the hydrolysis of the unreacted coupling reagent is accelerated in acidic conditions (Gilles, M. A., Hudson. A. Q. and Borders, C. L. (1990) 'Stability of water-soluble carbodiimides in aqueous solution', Analytical Biochemistry, Academic Press, 184(2), pp. 244-248. Moreover, the diffusivity of the coupling reagent is reduced in acidic conditions as the IPN loses its water content and its permeability is decreased. This results in further inhibition of the bulk reaction as the coupling reagents is consumed on the surface of the IPN. Taken together, molecules that are labile in aqueous solutions or form intermediate esters that are prone to hydrolysis at physiologic pH are not able to effectively derivatize the bulk of the PAA based IPNs and the modification remains localized in the surface of the IPN.

Various properties of the IPNs in physiologic conditions, including the lubricious properties, are dependent on the bulk derivatization of the material. The present inventors have found that IPN modification beyond a certain depth can be achieved only if a) the coupling reagent is water soluble and not liable in aqueous conditions, b) the intermediate ester is stable in physiologic pH, and c) the diffusion rate of the reactants is adequate to allow the reaction to occur before the intermediate ester gets hydrolyzed. Triazine based coupling reagents such as CDMT or DMTMM, are stable in aqueous conditions and have been used to derivatize macro-sugars such as hyaluronan (D'este M, Eglin D, Alini M. (2014). 'A systematic analysis of DMTMM vs EDC/NHS for ligation of amines to Hyaluronan in water', Carbohydrate Polymers, vol: 108 pp: 239-246). Reactions with DMTMM, where all the reactants are in solution, can have higher conversion rate than carboiimides. In this embodiment, the reaction conditions can be tuned to allow the efficient diffusion of the reactants before the hydrolysis of the intermediate ester that is formed between the triazine-based compound and the carboxylic acid groups of the secondary network of the IPN. Since the reaction is rate limited by diffusion and ester hydrolysis, the depth of the reaction can be controlled by varying the pH, by varying the reaction time, by the addition of the coupling reagent, or a combination any two or all three of the foregoing. The pH allows one to control the permeability of the IPN and the reactivity/hydrolysis rate of the intermediate ester. The reaction time allows one to control the amount of time needed for reactants to diffuse and react within the bulk of the material. The controlled addition of the coupling reagent allows the coupling reagent to be added at the same rate as the overall reaction rate, which combines reagent diffusion and reaction together with hydrogel swelling. By adjusting these parameters the derivatization of the IPN may be achieved in depths that range from a few microns to hundreds of microns or throughout the whole depth of the material.

Any number of initiators can be used such as photoinitiators (e.g., phenone-containing compounds), thermal initiators, or chemical initiators. Examples of thermal initiators include but are not limited to azo-compounds, peroxides (e.g., benzoyl peroxide), persulfates (e.g., potassium persulfate or ammonium persulfate), derivatives, or combinations thereof.

Variations of the crosslinking identity and density (e.g. 0.0001%-25% by mole crosslinking agent with respect to the monomer), initiator concentration (e.g. 0.0001%-0% by mole with respect to the monomer) molecular weight of precursor polymers, relative weight percent of polymers, light wavelength (UV to visible range), light intensity (0.01 mW/cm$^2$-5 W/cm$^2$), temperature, pH and ionic strength of swelling liquid, and the level of hydration.

The second network material can be synthesized in the absence of a crosslinking agent.

The water content of these materials can range between 2% to 99%.

Different components of the mixed anion IPN can be incorporated in combination with carboxylic-acid-group-containing monomers, such as vinyl alcohol, ethylene glycol-acrylate, 2-hydroxyethylacrylate. 2-hydroxyethylmethacrylate, acrylamide. N-isopropylacrylamide, dimethacrylamide, and combinations or derivatives thereof. Any monomer or combination of monomers can be used in conjunction with a suitable solvent as long as a carboxylic-acid-group-containing monomer is included and are able to enter (swell) the first polymer.

The mixed anion IPN can have incorporated either chemically or physically within its bulk or its surface certain additives such as antioxidants (e.g., Vitamin C, Vitamin E, or santowhite powder) and/or anti-microbial agents (e.g., antibiotics). These can be chemically linked to the material by, for example, esterification of the anti-oxidant with any vinyl-group containing monomer such as methacrylate, acrylate, acrylamide, vinyl, or allyl ether.

More than two networks (e.g., three or more) can also be formed, each of which are either crosslinked or uncrosslinked.

Other modifications will be apparent to those skilled in the art.

Further aspects of the present disclosure are shown in the paragraphs to follow.

Aspect 1. An implant comprising an ionic polymer that comprises underivatized carboxylic acid groups and amino-sulfonic-acid-derivatized carboxylic acid groups.

Aspect 2. The implant of aspect 1, wherein the underivatized carboxylic acid groups correspond to one or more of the following: underivatized acrylic acid monomers within the ionic polymer, underivatized methacrylic acid monomers within the ionic polymer, underivatized crotonic acid monomers within the ionic polymer, underivatized linolenic acid monomers within the ionic polymer, underivatized maleic acid monomers within the ionic polymer, and underivatized fumaric acid monomers within the ionic polymer, and wherein the amino-sulfonic-acid-derivatized carboxylic acid groups correspond one or more of the following: amino-sulfonic-acid-derivatized acrylic acid monomers within the ionic polymer, amino-sulfonic-acid-derivatized methacrylic acid monomers within the ionic polymer amino-sulfonic-acid-derivatized crotonic acid monomers within the ionic polymer, amino-sulfonic-acid-derivatized linolenic acid monomers within the ionic polymer, amino-sulfonic-acid-derivatized maleic acid monomers within the ionic polymer, and amino-sulfonic-acid-derivatized fumaric acid monomers within the ionic polymer.

Aspect 3. The implant of any of aspects 1-2, wherein the implant comprises a measurable amount of an amino sulfonic acid compound of the formula $(H_2N)_xR(SO_3H)_y$ or a salt thereof, where R is an organic moiety, x is a positive integer and y is a positive integer.

Aspect 4. The implant of aspect 3, wherein R is a hydrocarbon moiety.

Aspect 5. The implant of aspect 4, wherein the hydrocarbon moiety is an alkane moiety, an alkene moiety, an alkyne moiety, an aromatic moiety, or a hydrocarbon moiety having a combination of two or more of alkane, alkene, alkyne and aromatic substituents.

Aspect 6. The implant of any of aspects 4-5, wherein the hydrocarbon moiety is a C1-C12 hydrocarbon moiety.

Aspect 7. The implant of any of aspects 1-2, wherein the implant comprises a measurable amount of an amino sulfonic acid compound selected from taurine and taurine derivatives.

Aspect 8. The implant of any of aspects 1-7, wherein a concentration of the underivatized carboxylic acid groups and a concentration of the amino-sulfonic-acid-derivatized carboxylic acid groups are substantially constant throughout the implant.

Aspect 9. The implant of any of aspects 1-7, wherein a concentration of the underivatized carboxylic acid groups and/or a concentration of the amino-sulfonic-acid-derivatized carboxylic acid groups varies by at least +/−10% between two points in the implant.

Aspect 10. The implant of any of aspects 1-7, wherein the implant comprises a gradient in a concentration of the underivatized carboxylic acid groups and/or a gradient in a concentration of the amino-sulfonic-acid-derivatized carboxylic acid groups.

Aspect 11. The implant of aspect 10, wherein a concentration of the underivatized carboxylic acid groups decreases with increasing distance from at least one outer surface of the implant.

Aspect 12. The implant of aspect 10, wherein a concentration of the underivatized carboxylic acid groups increases with increasing distance from at least one outer surface of the implant.

Aspect 13. The implant of any of aspects 10-12, wherein a concentration of the amino-sulfonic-acid-derivatized carboxylic acid groups decreases with increasing distance from at least one outer surface of the implant.

Aspect 14. The implant of any of aspects 10-12, wherein a concentration of the amino-sulfonic-acid-derivatized carboxylic acid groups increases with increasing distance from at least one outer surface of the implant.

Aspect 15. The implant of any of aspects 1-14, wherein a molar ratio of the amino-sulfonic-acid-derivatized carboxylic acid groups to the underivatized carboxylic acid groups varies by at least +/−10% between two points in the implant.

Aspect 16. The implant of any of aspects 1-14, wherein a molar ratio of the amino-sulfonic-acid-derivatized carboxylic acid groups to the underivatized carboxylic acid groups decreases with increasing distance from at least on outer surface of the implant within the implant.

Aspect 17. Implant of any of aspects 1-14, wherein a molar ratio of the amino-sulfonic-acid-derivatized carboxylic acid groups to the underivatized carboxylic acid groups increases with increasing distance from at least on outer surface of the implant within the implant Aspect 18. The implant of any of aspects 1-14, wherein a molar ratio of the amino-sulfonic-acid-derivatized carboxylic acid groups to the underivatized carboxylic acid groups varies between one surface of the implant to and an opposing surface of the implant.

Aspect 19. The implant of any of aspects 1-18, wherein the implant comprises an interpenetrating or semi-interpenetrating polymer network that comprises a first polymeric network comprising a first polymer and a second polymeric network comprising the ionic polymer.

Aspect 20. The implant of aspect 19, wherein the first polymer is hydrophobic polymer.

Aspect 21. The implant of any of aspects 19-20, wherein the first polymer is a thermoplastic polymer.

Aspect 22. The implant of any of aspects 19-21, wherein the first polymer is a polyurethane.

Aspect 23. The implant of aspect 22, wherein the polyurethane is a polyether urethane.

Aspect 24. The implant of any of aspects 1-23, wherein the implant is configured to repair or replace cartilage in a joint in the body.

Aspect 25. The implant of aspect 24, wherein the joint in the body is selected from a knee joint, a condyle, a patella, a tibial plateau, an ankle joint, an elbow joint, a shoulder joint, a finger joint, a thumb joint, a glenoid, a hip joint, an intervertebral disc, an intervertebral facet joint, a labrum, a meniscus, a metacarpal joint, a metatarsal joint, a toe joint, a temporomandibular joint, and a wrist joint, including portions thereof.

Aspect 26. A method comprising reacting a solid article comprising a precursor polymer that comprises underivatized carboxylic acid groups with an amino sulfonic acid compound such that an amide bond is formed between the carboxylic acid groups of the precursor polymer and the amine groups of the amino sulfonic acid compound.

Aspect 27. The method of aspect 26, wherein the amino sulfonic acid compound is a compound of the formula $(H_2N)_xR(SO_3H)_y$, or a salt thereof, where R is an organic moiety, x is a positive integer and y is a positive integer.

Aspect 28. The method of aspect 26, wherein R is a hydrocarbon moiety.

Aspect 29. The method of aspect 28, wherein the hydrocarbon moiety is an alkane moiety, an alkene moiety, an alkyne moiety and aromatic moiety, or a hydrocarbon moiety comprising a combination of two or more of alkane, alkene, alkyne or aromatic substituents.

Aspect 30. The method of any of aspects 28-29, wherein the hydrocarbon moiety is a C1-C12 hydrocarbon moiety.

Aspect 31. The method of aspect 26, wherein the amino sulfonic acid is selected from taurine and taurine derivatives.

Aspect 32. The method of any of aspects 26-31, comprising contacting the solid article with the amino sulfonic acid compound such that the amino sulfonic acid compound is diffused into the solid article.

Aspect 33. The method of aspect 32, further comprising contacting the solid article with a coupling reagent such that the coupling reagent is diffused into the solid article.

Aspect 34. The method of aspect 33, wherein the coupling reagent is diffused into the solid article before the sulfonic acid compound is diffused into the solid article, wherein the coupling reagent is diffused into the solid article after the sulfonic acid compound is diffused into the solid article, or wherein the coupling reagent and the sulfonic acid compound are diffused into the solid article simultaneously.

Aspect 35. The method of any of aspects 33-34, wherein the coupling reagent is selected from a triazine-based coupling reagent, a carbodiimide coupling reagent, a phosphonium salt coupling reagent, an aminium salt coupling reagent, and a fluoroformamidinium coupling reagent.

Aspect 36. The method of any of aspects 33-34, wherein the coupling reagent is 4-(4,6-dimethoxy-1,3,5-triazin-2-yl)-4-methylmorpholinium chloride (DMTMM).

Aspect 37. The method of any of aspects 26-36, wherein the precursor polymer selected from polymers comprising one or more monomers selected from acrylic acid, methacrylic acid, crotonic acid, linolenic acid, maleic acid, and fumaric acid.

Aspect 38. The method of any of aspects 26-37, wherein the solid article comprises an interpenetrating or semi-interpenetrating polymer network that comprises a first polymeric network comprising a first polymer and a second polymeric network comprising the precursor polymer.

Aspect 39. The method of aspect 38, wherein the first polymer is hydrophobic polymer.

Aspect 40. The method of any of aspects 38-39, wherein the first polymer is a thermoplastic polymer.

Aspect 41. The method of any of aspects 38-40, wherein the first polymer is a polyurethane.

Aspect 42. The method of aspect 41, wherein the polyurethane is a polyether urethane.

Aspect 43. The method of any of aspects 26-42, wherein the implant is configured to repair or replace cartilage in a joint in the body.

Aspect 44. The method of aspect 43, wherein the joint in the body is selected from a knee joint, a condyle, a patella, a tibial plateau, an ankle joint, an elbow joint, a shoulder joint, a finger joint, a thumb joint, a glenoid, a hip joint, an intervertebral disc, an intervertebral facet joint, a labrum, a meniscus, a metacarpal joint, a metatarsal joint, a toe joint, a temporomandibular joint, and a wrist joint, including portions thereof.

Aspect 45. An implant comprising an ionic polymer and a divalent-cation-containing solution comprising one or more divalent metal cations, wherein the implant is at least partially immersed in the divalent-cation-containing solution.

Aspect 46. The implant of aspect 45, wherein the implant and the divalent-cation-containing solution are contained within a sterile package.

Aspect 47. The implant of any of aspects 44-46, wherein the divalent-cation-containing solution is a simulated body fluid that contains physiologic levels of ions found in the synovial fluid.

Aspect 48. The implant of any of aspects 44-47, wherein the divalent-cation-containing solution comprises 0.1 to 5 mM total divalent metal cations.

Aspect 49. The implant of any of aspects 44-48, wherein the divalent-cation-containing solution comprises calcium ions, magnesium ions or a combination of calcium and magnesium ions.

Aspect 50. The implant of any of aspects 44-48, wherein the divalent-cation-containing solution comprises calcium ions and magnesium ions.

Aspect 51. The implant of aspect 50, wherein the divalent-cation-containing solution comprises 0.5 to 2.0 mM calcium ions.

Aspect 52. The implant of any of aspects 50-51, wherein the divalent-cation-containing solution comprises 0.2 to 1.5 mM magnesium ions.

Aspect 53. The implant of any of aspects 44-52, wherein the divalent-cation-containing solution further comprises monovalent metal ions selected from sodium ions, potassium ions, or a combination of sodium and potassium ions.

Aspect 54. The implant of aspect 53, wherein the divalent-cation-containing solution contains 0 to 300 mM total monovalent metal cations.

Aspect 55. The implant of any of aspects 44-54, wherein the ionic polymer comprises carboxylic acid groups, sulfonic acid groups, or a combination of carboxylic acid groups and sulfonic acid groups.

Aspect 56. The implant of any of aspects 44-54, wherein the ionic polymer comprises carboxylic acid groups and sulfonic acid groups.

Aspect 57. The implant of any of aspects 44-56, wherein the implant comprises an interpenetrating or semi-interpenetrating polymer network that comprises a first polymeric network comprising a first polymer and a second polymeric network comprising the ionic polymer.

Aspect 58. The implant of aspect 57, wherein the first polymer is hydrophobic polymer.

Aspect 59. The implant of any of aspects 57-58, wherein the first polymer is a thermoplastic polymer.

Aspect 60. The implant of any of aspects 57-59, wherein the first polymer is a polyurethane.

Aspect 61. The implant of aspect 60, wherein the polyurethane is a polyether urethane.

Aspect 62. The implant of any of aspects 44-61, wherein the implant is selected to repair or replace cartilage in a joint in the body.

Aspect 63. The implant of aspects 62, wherein the joint is selected from a knee joint, a condyle, a patella, a tibial plateau, an ankle joint, an elbow joint, a shoulder joint, a finger joint, a thumb joint, a glenoid, a hip joint, an intervertebral disc, an intervertebral facet joint, a labrum, a meniscus, a metacarpal joint, a metatarsal joint, a toe joint, a temporomandibular joint and a wrist joint, including portions thereof.

EXAMPLES

Example 1

Figure 4:
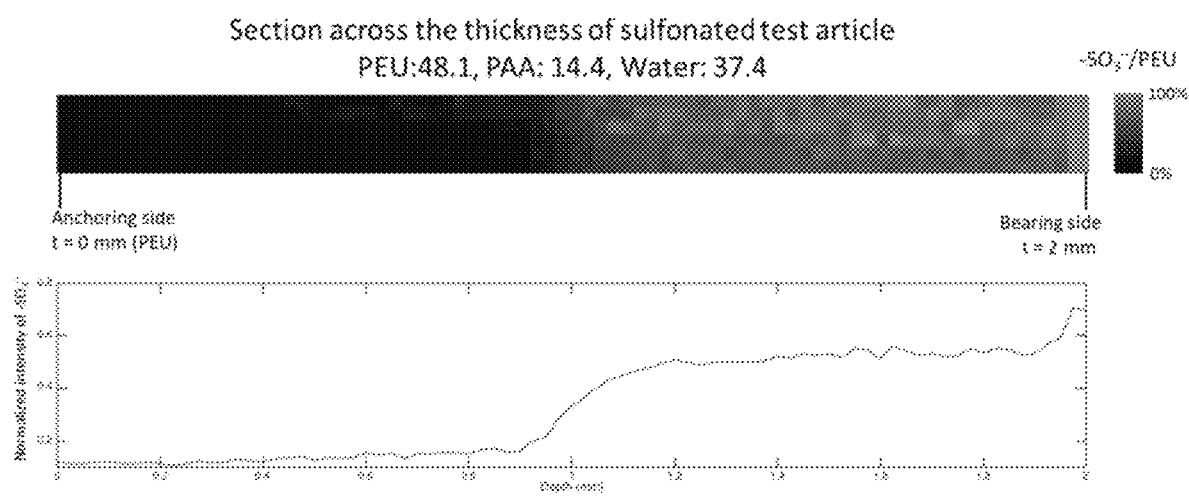
FIG. 4 is a graph of normalized sulfonate peak intensity of Raman microscopy spectra as a function of depth (mm) for a sulfonated gradient PEU-PAA in accordance with the present disclosure. Top: represents the intensity map of the ratio of the breathing mode of —SO$_3$ (1045 cm$^{-1}$) over one of the breathing modes of polyurethane (1640 cm$^{-1}$) throughout the depth (2 mm) of the sulfonated gradient PEU-PAA material. Bottom: Cumulative distribution of the ratio of the breathing mode of —SO$_3$ (1045 cm$^{-1}$) over one of the breathing modes of polyurethane (1640 cm$^{-1}$) over 200 um of thickness as a function of depth of the material.
Figure 5:
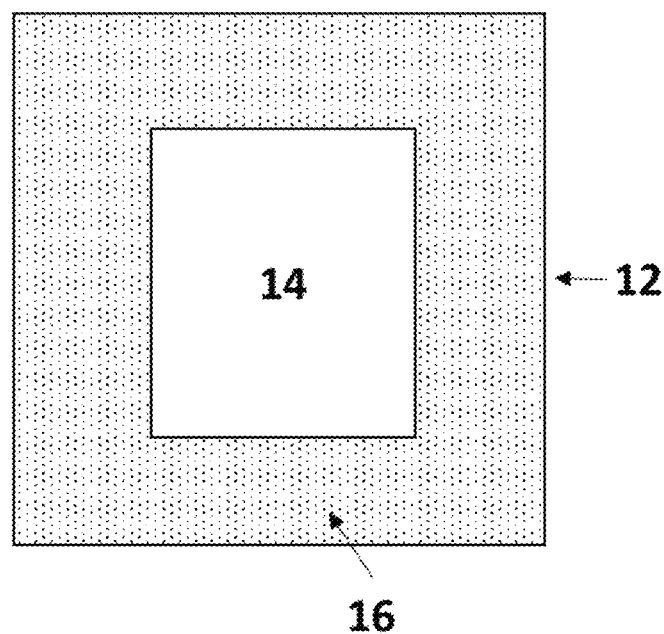
FIG. 5 is a schematic representation of a packaged article 10 according to an embodiment of the disclosure. The packaged article 10 includes an orthopedic implant comprising an interpenetrating network (IPN) or semi-IPN 14 and a divalent-cation-containing solution 16 contained within a sterile package 12.

The following description refers to a first exemplary embodiment of interpenetrating ionic polymer compositions with polyether urethane as the first network and polyacrylic acid as a second polymer network. The IPN is synthesized sequentially in two steps: test articles made from polyether urethane are impregnated in an aqueous solution of acrylic acid 70% (w/w %) which is supplemented with 5000 ppm and N-N'-methylenebis(acrylamide) and 1000 ppm 2-hydroxy-2-methylpropiophenone. The swollen articles are polymerized under ultraviolet irradiation (40 mW/cm$^2$) for 13 minutes and then neutralized at constant pH=7.4. The final composition of the IPN contained 37/19/45 (wt %) of PEU, PAA and H$_2$O, respectively. Test articles are incubated in taurine (aminoethanesulfonic acid) solution (320 mM) for 1 day, after which an equimolar amount of DMTMM ((4-(4,6-dimethoxy-1,3,5-triazin-2-yl)-4-methyl-morpholinium chloride) is added. The test articles are left to react for 48 h and they are washed with copious amounts of water for 4 d. This process is illustrated schematically in FIG. 2. After synthesis the chemical composition is assessed by elemental analysis (Table 1). The yield of sulfonation of PAA was 50%. Moreover, as shown in FIG. 4, the penetration of the amidation reaction reached halfway through (50%), or 1000 microns, the overall thickness of the test article (i.e., a 2 mm thick sample). In other words, if both sides participate in the diffusion of the reagents then the conversation can reach 100% and the material will be functionalized throughout the thickness of the PAA-PEU network. In contrast, when using a carbodiimide such as EDC under identical reaction conditions and reactants ratios the penetration and functionalization of the PAA-PEU network did not exceed 20%, or 400 microns in depth for a 2 mm thick sample. This difference in coupling efficiency between EDC and triazine coupling reagents has also been reported previously in the functionalization of hyaluronan macropolymers in aqueous conditions (D'este M, Eglin D, Alini M. (2014), 'A systematic analysis of DMTMM vs EDC/NHS for ligation of amines to Hyaluronan in water', Carbohydrate Polymers, vol: 108 pp: 239-246).

The following description refers to a second exemplary embodiment of interpenetrating ionic polymer compositions with polyether urethane as the first network and polyacrylic acid as a second polymer network. The IPN is synthesized sequentially in two steps: test articles made from polyether urethane are impregnated in an aqueous solution of acrylic acid 60% (w/w %) which is supplemented with 5000 ppm and N-N'-methylenebis(acrylamide) and 1000 ppm 2-hydroxy-2-methylpropiophenone. The swollen articles are polymerized under ultraviolet irradiation (40 mW/cm$^2$) for 13 minutes and then neutralized at constant pH=7.4. The final composition of the IPN contained 48/17/35 (wt %) of PEU, PAA and H$_2$O, respectively. Test articles are incubated in taurine solution (320 mM) for 1 day, after which an equimolar amount of DMTMM is added. The test articles are left to react for 48 h and they are washed with copious amounts of water for 4 d. After synthesis the chemical composition is assessed by elemental analysis (Table 1). The yield of sulfonation of PAA was 29%.

The following description refers to a third exemplary embodiment of interpenetrating ionic polymer compositions with polyether urethane as the first network and polyacrylic acid as a second polymer network. The IPN is synthesized sequentially in two steps: test articles made from polyether urethane are impregnated in an aqueous solution of acrylic acid 50% (w/w %) which is supplemented with 2000 ppm and N—N'-methylenebis(acrylamide) and 2000 ppm 2-hydroxy-2-methylpropiophenone. The swollen articles are polymerized under ultraviolet irradiation (40 mW/cm$^2$) for 13 minutes and then neutralized at constant pH=7.4. The final composition of the IPN contained 57/16/26 (wt %) of PEU, PAA and H$_2$O, respectively. Test articles are incubated in taurine solution (320 mM) for 1 day, after which an equimolar amount of DMTMM is added. The test articles are left to react for 48 h and they are washed with copious amounts of water for 4 d. After synthesis the chemical composition is assessed by elemental analysis (Table 1). The sulfonation yield PAA was 26%.

TABLE 1

Composition of exemplary sulfonated ionic interpenetrating networks

| PEU/PAA/H$_2$O (wt %) | Conditions | C | H | N | S | Yield (% sulfonation) |
|---|---|---|---|---|---|---|
| 57/16/26 | Control | 60.72 | 6.63 | 4.72 | N/A | N/A |
| 57/16/26 | Reacted with taurine | 60.00 | 6.86 | 5.85 | 1.51 | 26% |
| 48/17/35 | Control | 59.26 | 6.40 | 4.38 | N/A | N/A |
| 48/17/35 | Reacted with taurine | 57.70 | 6.86 | 6.07 | 1.88 | 29% |
| 37/19/45 | Control | 56.35 | 5.98 | 3.86 | N/A | N/A |
| 37/19/45 | Reacted with taurine | 54.27 | 6.53 | 6.24 | 3.94 | 50% |

Example 2

Gradient PEU-PAA formulations with range of PAA/PEU (w/w %) content from 17.6% to 29.9% were synthesized by following procedures along the lines described in Example 1. There is a linear correlation between the AA soaking solution and the PAA/PEU (w/w %), which allows determination of the final PAA/PEU percentage based on the initial soaking solution. Results are shown in Table 2

TABLE 2

Test samples produced for sulfonation and testing

| AA % (w/w)† | PEU (%) | PAA (%) | Water (%) | PAA/PEU (w/w %) |
|---|---|---|---|---|
| 45 | 68.10 | 12.0 | 19.9 | 17.6 |
| 50 | 65.50 | 12.1 | 22.4 | 18.5 |
| 55 | 59.50 | 12.2 | 28.3 | 20.5 |
| 57 | 53.40 | 13.6 | 33.0 | 25.5 |
| 60 | 53.1 | 14.5 | 32.5 | 27.3 |
| 63 | 49.2 | 14.2 | 36.6 | 28.9 |
| 65 | 48.1 | 14.4 | 37.4 | 29.9 |
| 70 | 38.5 | 15.6 | 45.9 | 40.7 |

†AA % (w/w) refers to the percentage of Acrylic Acid in water used for the synthesis of the gradient PEU-PAA test articles.

The gradient PEU-PAA formulations were then sulfonated in accordance with procedures along the lines of Example 1. The percent sulfonation was characterized by dry and wet weight increase along with elemental analysis to calculate sulfur content and sulfonation conversion. The data are summarized in Table 3. Sulfur content ranged from 0.5 to 2%, and the sulfonation conversion from 9% to 31%.

TABLE 3

Weight increase, sulfur content and sulfonation conversion for sulfonated gradient PEU-PAA

| AA (w/w %) | PAA/ PEU (w/w %) | Wet weight increase (%) | Dry weight increase (%) | Sulphur (%) | Sulfonation conversion (%) |
|---|---|---|---|---|---|
| 45 | 17.6 | 6.19 ± 1.21 | 6.06 ± 0.08 | 0.66 | 17 |
| 50 | 18.5 | 5.16 ± 0.5 | 5.15 ± 0.96 | 0.73 | 14 |
| 55 | 20.5 | 9.65 ± 0.43 | 8.23 ± 1.71 | 0.5 | 9 |
| 57 | 25.5 | 8.29 ± 0.54 | 9.11 ± 0.04 | 1.14 | 21 |
| 60 | 27.3 | 11.31 ± 0.74 | 11.28 ± 0.03 | 1.35 | 22 |
| 63 | 28.9 | 11.37 ± 1.12 | 11.87 ± 0.76 | 1.41 | 27 |
| 65 | 29.9 | 15.31 ± 1.12 | 12.75 ± 0.22 | 1.66 | 31 |
| 70 | 40.7 | 16.77 ± 0.9 | 14.45 ± 2.55 | 1.64 | 11 |

The sulfonated gradient PEU-PAA materials exhibited a trend of higher weight increase after sulfonation with an increase in PAA/PEU w/w %, suggesting that with increasing PAA content, more carboxylic groups from PAA react with the taurine to introduce sulfonate groups. The weight increase (both wet and dry) for sulfonated gradient PEU-PAA was found to be linear as a function of PAA/PEU content. The dry weight increase is believed to result from the addition of taurine molecules to the PAA backbone via sulfonation reaction, while the wet weight increase is believed to result from the ability of sulfonated gradient PEU-PAA to retain water content.

Elemental analysis was performed to get the carbon, nitrogen, hydrogen, and sulfur contents from the sulfonated test articles. This data was used to calculate the conversion of carboxylic groups into sulfonate groups. As seen from Table 3, the sulfur content/sulfonation conversion increased with the increasing of PAA/PEU percentage. This indicates that as the number of carboxyl group per unit weight increase, more taurine could be attached.

The last synthesis step of sulfonated gradient PEU-PAA test articles involved equilibrating in simulated body fluid (SBF, 1.2 mM $Ca^{2+}$, 0.6 mM $Mg^{2+}$, 154 mM NaCl) before gamma irradiation. The final composition for all the synthesized materials after SBF equilibration were calculated and listed in Table 4.

TABLE 4

Composition of sulfonated gradient PEU-PAA after equilibration in SBF

| AA (w/w %) | PEU (%) | Sulfonated PAA + PAA (%) | Water (%) | (Sulfonated PAA + PAA)/PEU (w/w %) |
|---|---|---|---|---|
| 45 | 65.7 | 16.7 | 17.6 | 25 |
| 50 | 62.2 | 18.3 | 19.5 | 29 |
| 55 | 57.3 | 18.8 | 23.9 | 33 |
| 57 | 51.7 | 20.5 | 27.8 | 40 |
| 60 | 50.9 | 23.0 | 26.1 | 45 |
| 63 | 46.7 | 22.3 | 31.0 | 48 |
| 65 | 44.5 | 22.8 | 32.7 | 51 |
| 70 | 34.9 | 23.7 | 41.4 | 68 |

Tensile, compressive, tear properties of sulfonated gradient PEU-PAA test articles across a range of PAA content were evaluated. The data is summarized in Tables 5 through 7. To allow for direct comparison of the material properties between gradient PEU-PAA formulations and a non-sulfonated gradient PEU-PAA formulation using a common variable, PAA/PEU percentage is used as the independent variable for the following reasons: (a) the same sulfonation conditions were used across all synthesized materials irrespectively of their PAA/PEU (w/w %). (b) sulfonation was indirectly controlled by the level of PAA/PEU (w/w %) (see Table 3), and (c) material synthesized with the same initial conditions had statistically similar mechanical properties irrespectively of the sulfonation process or the sulfur content.

The tensile properties for all formulations are listed in Table 5 and Table 5.1. The Ultimate tensile strength (UTS) was found to decrease with an increase in PAA/PEU w/w %. This is attributed to an increase in water content as a function of PAA/PEU w/w % (Table 3) which results in weaker materials.

TABLE 5

Tensile Strength of sulfonated gradient PEU-PAA and non-sulfonated gradient PEU-PAA.

| Formulation | PAA/ PEU w/w % | Sulfonation conversion (%) | Ultimate Tensile Strength (MPa) |
|---|---|---|---|
| Sulfonated gradient PEU-PAA | 17.6 | 17 | 91.3 ± 10.5 |
| | 22.2 | 14 | 78.7 ± 8.7 |
| | 20.5 | 9 | 61.5 ± 6.5 |
| | 25.5 | 21 | 54.8 ± 7.7 |
| | 27.2 | 22 | 40.7 ± 4.8 |
| | 28.9 | 27 | 34.5 ± 3.7 |
| | 30 | 31 | 33.8 ± 5.8 |
| | 40.7 | 11 | 22.9 ± 1.2 |
| Non-sulfonated gradient PEU-PAA | 40.7 | N/A | 50.2 ± 3.1 |

TABLE 5.1

Tensile properties of sulfonated gradient PEU-PAA and Non-sulfonated gradient PEU-PAA

| Formulation | PAA/PEU w/w % | Ultimate tensile strain (%) | Tensile modulus (MPa) | Tangent tensile modulus (MPa) |
|---|---|---|---|---|
| Sulfonated gradient PEU-PAA | 17.6 | 223.8 ± 52.3 | 37.1 ± 2.2 | 37.1 ± 2.2 |
| | 22.2 | 189.8 ± 51.1 | 37.8 ± 1.3 | 37.8 ± 1.3 |
| | 20.5 | 169.7 ± 40.1 | 34.5 ± 1.1 | 34.5 ± 1.1 |
| | 25.5 | 153.0 ± 46.5 | 33.4 ± 1.4 | 33.4 ± 1.4 |
| | 27.2 | 128.3 ± 31.5 | 32.2 ± 2.0 | 32.2 ± 2.0 |
| | 28.9 | 110.6 ± 22.5 | 31.6 ± 2.0 | 31.6 ± 2.0 |
| | 30 | 117.3 ± 50.7 | 29.5 ± 1.7 | 29.5 ± 1.7 |
| | 40.7 | 95.2 ± 12.8 | 24.6 ± 0.5 | 24.6 ± 0.5 |
| Non-sulfonated gradient PEU-PAA | 40.7 | 181.0 ± 32.7 | 29.0 ± 0.3 | 29.0 ± 0.3 |

Similar trends were observed for all other tensile properties evaluated. Specifically, the ultimate true strain which captures the maximum elongation of the material before failure was reduced as a function of the PAA/PEU w/w %, ranging from 223.8±52.3% for the formulation with the lowest (17.6%) PAA/PEU w/w %, to 95.2±12.8% for the formulation with highest (40.7%) (Table 5.1). The ultimate true strain of non-sulfonated gradient PEU-PAA was 181.0±32.7%, which is almost 2 times higher than the sulfonated counterpart (95.2±12.8%) with the same PAA/PEU w/w %. This is attributed to the sulfonated gradient PEU-PAA formulation with 40.7% PAA/PEU w/w % having more water (41.4%—see Table 3) than the non-sulfonated gradient PEU-PAA (36.7%—see Table 3). Moreover, high variance of the ultimate true strain was observed which is attributed to the stochasticity of the material failure under tension which is affected by material and test article imperfections.

The tensile modulus (Young's modulus) that defines the relationship between stress and strain in the linear elastic region, decreased exponentially as a function of increasing PAA/PEU w/w %. The tensile modulus (32.5±0.8 MPa) for the formulation with the 40.7 (highest) PAA/PEU w/w % decreased significantly ($p<0.01$) from the previous formulation (48.4±2.8 MPa) with 30% PAA/PEU w/w %, which suggests that above this threshold the tensile modulus drops rapidly. Moreover, similar to the trends seen in ultimate tensile strength and tensile strain, the tensile modulus of the non-sulfonated gradient PEU-PAA, was higher (46.4±2.3) than the sulfonated gradient PEU-PAA with the same PAA/PEU w/w %.

Similar to UTS, the tangent tensile modulus at 30% strain (see Table 5.1), which is useful in describing the behavior of a material that has been stressed beyond the elastic region and reaches plastic deformation, decreased with increasing PAA/PEU w/w %. The tangent tensile modulus was 37.1±2.2 MPa for test articles with lowest (17.6%) PAA/PEU w/w % and was reduced to 24.6±0.5 MPa for formulation with highest (40.7%) PAA/PEU w/w %. In contrast, the tangent tensile modulus for non-sulfonated gradient PEU-PAA was 29.0±0.35 MPa, which indicates that as materials are plastically deformed both sulfonated and non-sulfonated formulations with the same PAA/PEU w/w % have a similar deformation rate.

Taking all the tensile properties together, in order to obtain tensile properties similar to non-sulfonated gradient PEU-PAA, lower levels of PAA compared to non-sulfonated gradient PEU-PAA can be used for sulfonated gradient PEU-PAA.

The compressive properties of all formulations are listed in Table 6 and Table 6.1. All formulations were above a desired preliminary specification of 25.4 MPa for ultimate compressive strength. None of the sulfonated gradient PEU-PAA samples failed under compression even at high strain (>60% of true compressive strain). As the materials do not fail under compression, there was no specific trend established for the ultimate compressive strength and the ultimate compressive strain.

TABLE 6

Compressive strength properties of sulfonated gradient PEU-PAA and non-sulfonated gradient PEU-PAA

| Formulation | PAA/PEU w/w % | Sulfonation conversion (%) | Ultimate Compressive Strength (MPa) |
|---|---|---|---|
| Sulfonated gradient PEU-PAA | 17.6 | 17 | 245.5 ± 22.8 |
| | 22.2 | 14 | 228.8 ± 46.4 |
| | 20.5 | 9 | 161.6 ± 37.6 |
| | 25.5 | 21 | 277.9 ± 60.9 |
| | 27.2 | 22 | 275.9 ± 51.6 |
| | 28.9 | 27 | 251.6 ± 42.4 |
| | 30 | 31 | 242.8 ± 28.7 |
| | 40.7 | 11 | 302.1 ± 33.4 |
| Non-sulfonated gradient PEU-PAA | 40.7 | N/A | 332.8 ± 16.7 |
| Preliminary Specification | N/A | N/A | >25.4 MPa |

TABLE 6.1

Compressive properties of sulfonated gradient PEU-PAA and Non-sulfonated gradient PEU-PAA

| Formulation | PAA/PEU w/w % | Ultimate compressive strain (%) | Compressive modulus (MPa) | Tangent compressive modulus (MPa) |
|---|---|---|---|---|
| Sulfonated gradient PEU-PAA | 17.6 | 61.6 ± 2.1 | 111.1 ± 11.5 | 177.8 ± 8.7 |
| | 22.2 | 59.9 ± 2.6 | 86.1 ± 5.7 | 182.3 ± 13.9 |
| | 20.5 | 56.1 ± 2.4 | 80.4 ± 4.1 | 157.3 ± 7.1 |
| | 25.5 | 61.4 ± 1.7 | 72.0 ± 9.8 | 163.0 ± 11.2 |
| | 27.2 | 56.8 ± 3.4 | 69.4 ± 17.4 | 161.7 ± 11.4 |
| | 28.9 | 61.3 ± 1.9 | 68.7 ± 7.9 | 155.9 ± 5.1 |
| | 30 | 61.6 ± 0.8 | 59.7 ± 2.0 | 139.6 ± 9.2 |
| | 40.7 | 60.1 ± 6.7 | 50.4 ± 10.6 | 145.7 ± 19.5 |
| Non-sulfonated gradient PEU-PAA | 40.7 | 64.0 ± 0.1 | 69.3 ± 2.9 | 155.9 ± 4.3 |

The compressive strength of non-sulfonated gradient PEU-PAA was 332.8±16.7 MPa and it was higher than all sulfonated gradient PEU-PAA formulations. As the materials did not fail under compression direct comparison of the compressive strength is not possible, therefore the materials were re-evaluated in dynamic compression.

The compressive modulus (Young's modulus for compression) that measures the stiffness of a solid material under compression in the linear elastic region displayed an exponential decrease as a function of increasing PAA/PEU w/w %, similar to the tensile modulus. The compressive modulus progressively decreased from 111.1±11.5 MPa for the formulation with lowest (17.6) PAA/PEU w/w % to 50.4*10.6 MPa for the formulation with the highest (40.7) PAA/PEU w/w %. These values are of the same order of magnitude as human articular cartilage 8.1-15.3 MPa (Parsons, J. R. (1998) 'Cartilage', in *Handbook of Biomaterial Properties*.

Boston, Mass.: Springer US, pp. 40-47. doi: 10.1007/978-1-4615-5801-9_4), which shows that sulfonated formulations have comparable physiologic stiffnesses.

Similar to the tangent tensile modulus, the tangent compressive modulus demonstrates the behavior of the material beyond the elastic region and the rate at which the material experiences plastic deformation. The tangent compression modulus was 177.8+8.7 MPa for test articles with lowest (17.6%) PAA/PEU w/w % and was reduced to 145.7±19.5 MPa for the formulation with highest (40.7%) PAA/PEU w/w %. The tangent compressive modulus for non-sulfonated gradient PEU-PAA was 155.9±4.3, which corresponds to sulfonated materials that have less PAA/PEU w/w % or higher PEU content.

Tear strength followed a similar trend as the tensile and compression properties and decreased as a function of increasing PAA/PEU w/w % (Table 7). The tear strength values that were acquired for the range of the synthesized sulfonated gradient PEU-PAA ranged from 28.8±2.2 N/mm to 70±3.8 N/mm, respectively. Tear strength of the Non-sulfonated gradient PEU-PAA was 57.7±2.5 N/mm, which is similar to sulfonated materials that have less PAA/PEU w/w % or higher PEU content.

TABLE 7

Tear Strength properties for sulfonated gradient PEU-PAA formulations and non-sulfonated gradient PEU-PAA

| Formulation | PAA/PEU w/w % | Sulfonation conversion (%) | Tear Strength (N/mm) |
|---|---|---|---|
| Sulfonated gradient PEU-PAA | 17.6 | 17 | 70. ± 3.8 |
| | 22.2 | 14 | 62.2 ± 3.2 |
| | 20.5 | 9 | 60.9 ± 3.3 |
| | 25.5 | 21 | 54.6 ± 1.4 |
| | 27.2 | 22 | 54.8 ± 3.7 |
| | 28.9 | 27 | 48.7 ± 2.9 |
| | 30.0 | 31 | 43.7 ± 2.9 |
| | 40.7 | 11 | 28.8 ± 2.2 |
| Non-sulfonated gradient PEU-PAA | 40.7 | N/A | 57.7 ± 2.5 |

As part of the synthesis, all formulations including non-sulfonated gradient PEU-PAA were equilibrated in SBF prior to packaging and gamma irradiation. The coefficient of friction (COF) values are listed in Table 8. It was observed that all sulfonated gradient PEU-PAA demonstrated similar friction values (0.034±0.007) regardless of their PAA/PEU content and sulfur content, which are significantly lower (p<0.01) than that of non-sulfonated gradient PEU-PAA.

Preliminary assessment of the sulfonation distribution across the thickness of the material, demonstrated that sulfonation was higher on the bearing side than the bulk and it was progressively reduced with the increasing depth as seen in FIG. 4 (sulfonated gradient PEU-PAA formulation having 48.1 wt % PEU, 14.4 wt % PAA, 37.4 wt % water). The degree of sulfonation is determined by measuring the normalized intensity of the sulfonate peak at 1045 $cm^{-1}$ relative to the carbonyl peak at 1640 $cm^{-1}$ using Raman spectroscopy.

Since the sulfonation reaction conditions were the same for all sulfonated materials, all sulfonated gradient PEU-PAA formulations are expected to have the highest concentration of sulfonate moieties on the bearing surface irrespectively of their PAA/PEU percentage. In contrast, non-sulfonated gradient PEU-PAA equilibrated in SBF exhibited friction coefficient above 0.1. This suggests that the sulfonation process renders the materials to be lubricious with a low coefficient of friction.

TABLE 8

Friction coefficient of the sulfonated gradient PEU-PAA formulations and Non-sulfonated gradient PEU-PAA

| Formulation | PAA/PEU w/w % | Sulfonation conversion (%) | Friction Coefficient |
|---|---|---|---|
| Sulfonated gradient PEU-PAA | 17.6 | 17 | 0.045 ± 0.004 |
| | 20.5 | 9 | 0.029 ± 0.003 |
| | 25.5 | 21 | 0.032 ± 0.005 |
| | 27.2 | 22 | 0.033 ± 0.004 |
| | 28.9 | 27 | 0.032 ± 0.002 |
| | 30 | 31 | 0.044 ± 0.011 |
| | 40.7 | 11 | 0.044 ± 0.008 |
| Non-sulfonated gradient PEU-PAA | 40.7 | N/A | 0.130 ± 0.033 |

The friction coefficient was also assessed for a group of sulfonated gradient PEU-PAA with similar PAA/PEU w/w % (22.9%) and sulfur content (1.05%). The friction coefficient for this formulation was 0.042*0.001 (n=3).

Thus, the effects of a range of PAA/PEU percent from 17.6% to 40.7% and sulfonation conversion from 9 to 31% on mechanical and frictional properties were assessed. The formulations were compared to non-sulfonated gradient PEU-PAA formulation (40.7% PAA/PEU and no sulfonation) to evaluate the effects of sulfonation on properties. All IPNs had mechanical properties that met or exceeded the current preliminary specifications. The formulations with lower PAA/PEU w/w % were more rigid than formulations with higher PAA/PEU w/w %, and this effect is attributed to the increase in water content after sulfonation.

All sulfonated formulations had a low (<0.045) coefficient of friction (COF) in SBF compared to non-sulfonated gradient PEU-PAA (0.1), which indicates that lubriciousness of the surface is independent of the % sulfonation over the range of 9-31% studied. All sulfonated formulations showed similar COF values suggesting that the percent sulfonation or PAA content over the range studied was sufficient to create a highly lubricious surface in the presence of SBF.

To further test the ability of the sulfonated formulations of Example 3 to withstand the effect of divalent ions under physiologic conditions, a test that quantifies water loss over a broad physiologic range of total divalent ion concentrations was developed. This test is reported in Ising, H., Bertschat, F. Gunther, T., Jeremias. E., Jeremias, A., & Ising, 1. (1995), "Measurement of Free Magnesium in Blood, Serum and Plasma with an Ion-Sensitive Electrode." *Clinical Chemistry and Laboratory Medicine.* 33(6), 365-372 and Fijorek, K., Pusküllüoglu, M., Tomaszewska. D., Tomaszewski. R., Glinka. A., & Polak, S. (2014), "Serum potassium, sodium and calcium levels in healthy individuals—literature review and data analysis," *Folia Medica Cracoviensia,* 54(1), 53-70, and it is used to determine the sensitivity of the material within the hypo- and hyper-physiological range by monitoring the percentage of water lost per mM of divalent ions. Sulfonated gradient PEU-PAA and non-sulfonated gradient PEU-PAA test articles that were equilibrated in SBF (1.8 mM of total divalent ion cations), were submitted to buffers that range from 1.4 mM (hypo-physiological) to 2.2 mM (hyper-physiological) of total divalent ions and their water loss was measured after reaching equilibrium. For each concentration, a line was fitted and the slope of each line was calculated (Table 9). The divalent ion sensitivity (slope of the fitted line) is depicted for a representative set of tested formulation (FIGS. 3A-3E). The sensitivity ranged from −1.32%/mM (percent water loss per millimolar of total divalent cations) for the formulation with 17.6% PAA/PEU w/w %, down to −1.86%/mM of the formulation with 40.7% PAA/PEU w/w %.

TABLE 9

Percent water loss per mM of total divalent ions for sulfonated gradient PEU-PAA and non-sulfonated gradient PEU-PAA (n = 5).

| Formulation | PAA/PEU (w/w %) | Sulfonation conversion (%) | % water loss per mM of total divalent ions | P-value* |
|---|---|---|---|---|
| Sulfonated gradient PEU-PAA | 17.6 | 17 | −1.32 | 0.0328 |
| | 22.2 | 14 | −1.33 | 0.0265 |
| | 20.5 | 9 | 0.15 | 0.5203 |
| | 25.5 | 21 | −0.65 | 0.0495 |
| | 27.2 | 22 | −0.09 | 0.6459 |
| | 28.9 | 27 | −2.10 | 0.1231 |
| | 30.0 | 31 | 0.99 | 0.4095 |
| | 40.7 | 11 | −1.84 | 0.0004 |
| Non-sulfonated gradient PEU-PAA | 40.7 | N/A | −1.68 | 0.0145 |

*P-value refers to the null hypothesis that the slope is indifferent from zero (% water loss/mM ≠ 0)

One desirable characteristic of a synthetic cartilage implant is the ability of the of the material to preserve its water content in physiologic conditions. Devices packaged in phosphate buffer saline, once implanted in humans, are exposed to the divalent-ion-rich environment of synovial fluid (~1.2 mM $Ca^{+2}$, 0.6 mM $Mg^{+2}$). It is known that sodium salts of polymeric weak acids such as PAA have high selectivity towards $Ca^{+2}$ and $Mg^{+2}$ which ultimately leads to the displacement of sodium ions (Dorfner, K. (1991) "Ion exchangers," Berlin, N.Y.: DE GRUYTER. doi: 10.1515/9783110862430). Since one molecule of $Ca^{+2}$ and $Mg^{+2}$ can bind two carboxylate groups, PAA chains can become cross-linked through ionic interactions. This can lead to shrinkage of the PAA network and hence loss of water in vivo.

In the present Example, all sulfonated gradient PEU-PAA formulations that were exposed to SBF showed less water loss after equilibration than that of the non-sulfonated gradient PEU-PAA. Moreover, the water loss was further minimized within the range of PAA/PEU percentage that has mechanical properties equivalent to the non-sulfonated gradient PEU-PAA. In particular, sulfonated formulations within the range of 25.5 to 30% PAA/PEU w/w % and/or sulfonation levels between 21-31% exhibited less water loss (6.5±0.6 to 9.2±10.5%) than the non-sulfonated gradient PEU-PAA (13.8±1.0), and no measurable change in weight loss over the range of physiologic ion variation tested.

The invention claimed is:

1. A packaged article comprising an orthopedic implant and a divalent-cation-containing solution contained within a sterile package, wherein the orthopedic implant comprises an interpenetrating polymer network (IPN) or semi-IPN that comprises a first polymeric network comprising a hydrophobic thermoset or thermoplastic polymer and a second polymeric network comprising a polymer comprising carboxylic acid groups that are underivatized or sulfonic-acid-derivatized, and the divalent-cation-containing solution comprises 0.1 to 5 mM divalent metal cations comprising $Ca^{2+}$.

2. The packaged article of claim 1, wherein the IPN or semi-IPN has first and second surfaces, wherein the first surface has a composition corresponding to the hydrophobic thermoset or thermoplastic polymer and wherein a concentration of the carboxylic acid groups is at a maximum at the second surface and decreases to zero or substantially zero concentration within a bulk of the IPN or semi-IPN, and the carboxylic acid groups are underivatized carboxylic acid groups, sulfonic-acid-derivatized carboxylic acid groups, or a mixture thereof.

3. The packaged article of claim 2, wherein the polymer having carboxylic acid groups comprises one or more monomers selected from acrylic acid, methacrylic acid, crotonic acid, linolenic acid, maleic acid, and fumaric acid.

4. The packaged article of claim 3, wherein the carboxylic acid groups are underivatized.

5. The packaged article of claim 3, wherein the carboxylic acid groups include sulfonic-acid derivatized carboxylic acid groups.

6. The packaged article of claim 5, wherein the sulfonic-acid-derivatized carboxylic acid groups are amino-sulfonic-acid-derivatized carboxylic acid groups.

7. The packaged article of claim 6, wherein the second polymeric network comprises a measurable amount of an amino sulfonic acid compound of the formula $(H_2N)_xR(SO_3H)_y$, or a salt thereof, where R is an organic moiety, x is a positive integer, and y is a positive integer.

8. The packaged article of claim 7, wherein R is a hydrocarbon moiety.

9. The packaged article of claim 8, wherein the hydrocarbon moiety is an alkane moiety, an alkene moiety, an alkyne moiety, an aromatic moiety, or a hydrocarbon moiety having a combination of two or more of alkane, alkene, alkyne, and aromatic substituents.

10. The packaged article of claim 9, wherein the hydrocarbon moiety is a $C_1$-$C_{12}$ hydrocarbon moiety.

11. The packaged article of claim 10, wherein the amino sulfonic acid is taurine or a derivative thereof.

12. The packaged article of claim 6, wherein the carboxylic acid groups further include underivatized carboxylic acid groups.

13. The packaged article of claim 6, wherein the IPN or semi-IPN comprises a gradient in a concentration of the sulfonic-acid-derivatized carboxylic acid groups.

14. The packaged article of claim 13, wherein a concentration of the sulfonic-acid-derivatized carboxylic acid groups decreases by at least 10% from a point on the second surface of the IPN or semi-IPN to at least one point in the bulk of the IPN or semi-IPN.

15. The packaged article of claim 13, wherein a concentration of the sulfonic-acid-derivatized carboxylic acid groups does not vary by more than +/−10% between any two points in the IPN or semi-IPN.

16. The packaged article of claim 12, wherein the IPN or semi-IPN comprises a gradient in a concentration of the sulfonic-acid-derivatized carboxylic acid groups.

17. The packaged article of claim 16, wherein a concentration of the sulfonic-acid-derivatized carboxylic acid groups and a concentration of the underivatized carboxylic acid groups do not vary by more than +/−10% between any two points in the IPN or semi-IPN.

18. The packaged article of claim 16, wherein the second polymeric network comprises a gradient in a concentration of the sulfonic-acid-derivatized carboxylic acid groups and a gradient in a concentration of the underivatized carboxylic acid groups.

19. The packaged article of claim 16, wherein a concentration of the sulfonic-acid-derivatized carboxylic acid groups decreases by at least 10% from a point on the second surface of the IPN or semi-IPN to at least one point in a bulk of the IPN or semi-IPN, and wherein a concentration of the underivatized carboxylic acid groups increases by at least 10% from the point on the second surface of the IPN or semi-IPN to at least one point in the bulk of the IPN or semi-IPN.

20. The packaged article of claim 16, wherein a molar ratio of the sulfonic-acid-derivatized carboxylic acid groups to the underivatized carboxylic acid groups decreases by at least 10% from a point on the second surface of the IPN or semi-IPN to at least one point in the bulk of the IPN or semi-IPN.

21. The packaged article of claim 1, wherein the first polymeric network comprises polyurethane.

22. The packaged article of claim 21, wherein the first polymeric network comprises polyetherurethane.

23. The packaged article of claim 1, wherein the implant is configured to repair or replace cartilage in a joint in the body.

24. The packaged article of claim 23, wherein the joint in the body is a knee joint, a condyle, a patella, a tibial plateau, an ankle joint, an elbow joint, a shoulder joint, a finger joint, a thumb joint, a glenoid, a hip joint, an intervertebral disc, an intervertebral facet joint, a labrum, a meniscus, a metacarpal joint, a metatarsal joint, a toe joint, a temporomandibular joint, a wrist joint, or a portion thereof.

\* \* \* \* \*